United States Patent
Popovtzer et al.

(10) Patent No.: US 12,226,496 B2
(45) Date of Patent: Feb. 18, 2025

(54) POLYMERIC CORE-SHELL PARTICLES

(71) Applicant: BAR-ILAN UNIVERSITY, Ramat Gan (IL)

(72) Inventors: Rachela Popovtzer, Givat Shmuel (IL); Chen Tzror-Azankot, Rishon Leztion (IL); Menachem Motiei, Ashdod (IL)

(73) Assignee: BAR-ILAN UNIVERSITY, Ramat Gan (IL)

( * ) Notice: Subject to any disclaimer, the term of this patent is extended or adjusted under 35 U.S.C. 154(b) by 0 days.

(21) Appl. No.: 17/051,687

(22) PCT Filed: Apr. 30, 2019

(86) PCT No.: PCT/IL2019/050480
§ 371 (c)(1),
(2) Date: Oct. 29, 2020

(87) PCT Pub. No.: WO2019/211843
PCT Pub. Date: Nov. 7, 2019

(65) Prior Publication Data
US 2021/0228750 A1 Jul. 29, 2021

Related U.S. Application Data

(60) Provisional application No. 62/664,302, filed on Apr. 30, 2018.

(51) Int. Cl.
*A61K 51/04* (2006.01)
*A61K 49/00* (2006.01)
*A61K 51/12* (2006.01)

(52) U.S. Cl.
CPC ...... *A61K 51/0482* (2013.01); *A61K 49/0002* (2013.01); *A61K 51/0491* (2013.01); *A61K 51/1234* (2013.01)

(58) Field of Classification Search
CPC ............ A61K 51/0482; A61K 49/0002; A61K 51/0491; A61K 51/1234
USPC ....................................... 424/1.65
See application file for complete search history.

(56) References Cited

U.S. PATENT DOCUMENTS

| | | | |
|---|---|---|---|
| 2011/0020243 A1* | 1/2011 | Aydogan ............ | A61K 49/0485 424/9.42 |
| 2011/0044911 A1 | 2/2011 | Akhtari et al. | |
| 2012/0107232 A1* | 5/2012 | Hsu .................. | A61P 35/00 424/1.21 |
| 2015/0343084 A1 | 12/2015 | Dilley | |
| 2017/0189560 A1 | 7/2017 | Popovtzer et al. | |

FOREIGN PATENT DOCUMENTS

| | | | | |
|---|---|---|---|---|
| WO | 2010094043 A2 | 8/2010 | | |
| WO | WO-2011046842 A1 * | 4/2011 | ........... | A61K 47/488 |
| WO | 2016046793 A2 | 3/2016 | | |
| WO | 2017221270 A1 | 12/2017 | | |

OTHER PUBLICATIONS

Zhu et al. Molecules 2013, 18, 6425-6438. (Year: 2013).*
Zhang et al. Cell. Mol. Bioengin. 2017, 10, 275-294. (Year: 2017).*
Hormann et al. J. Control. Rel. 2016, 223, 85-98. (Year: 2016).*
Yeeprae et al. (J. Control Rel. 114 (2006) 193-201. (Year: 2006).*
Chen et al. Mol. Cell Biochem. (2017) 436:79-86. (Year: 2017).*
Malinge J. et al., Liposomes for PET and MR Imaging and for Dual Targeting (Magnetic Field/Glucose Moiety): Synthesis, Properties, and in Vivo Studies. Molecular Pharmaceutics, vol. 14, Issue 2, 2017, pp. 406-414.
Motiei M. et al., Differentiating Between Cancer and Inflammation: A Metabolic-Based Method for Functional Computed Tomography Imaging. ACS Nano, vol. 10, Issue 3, 2016, pp. 3469-3477.
Oku N., Delivery of contrast agents for positron emission tomography imaging by liposomes. Advanced Drug Delivery Reviews, vol. 37, Issues 1-3, 1999, pp. 53-61.
Pitchaimani A. et al., Design and characterization of gadolinium infused theranostic liposomes. RSC Advances, vol. 6, Issue 43, 2016, pp. 1-9.
PCT Preliminary Report on Patentability for International Patent Application No. PCT/IL2019/050480, dated Nov. 3, 2020, 9 pp.
PCT Search Report for International Patent Application No. PCT/IL2019/050480, mailed Aug. 8, 2019, 5 pp.
PCT Written Opinion for International Patent Application No. PCT/IL2019/050480, mailed Aug. 8, 2019, 8 pp.

* cited by examiner

*Primary Examiner* — Johann R Richter
*Assistant Examiner* — Sean R Donohue
(74) *Attorney, Agent, or Firm* — The Roy Gross Law Firm, LLC; Roy Gross

(57) ABSTRACT

A nanoparticle having a lipidic core, wherein the nanoparticle is linked via first polymeric linkers to a glucose molecules, and is further linked via second polymeric linkers to chelating agents, and wherein a weight ratio of the chelating agents to the nanoparticle is 1:20 to 1:80, respectively, is disclosed. Uses of the nanoparticle, particularly for imaging a tumor in a mammal, are further disclosed.

18 Claims, 11 Drawing Sheets

POLYMERIC CORE-SHELL PARTICLES

CROSS REFERENCE TO RELATED APPLICATIONS

This application is a National Phase of PCT Patent Application No. PCT/IL2019/050480 having International filing date of Apr. 30, 2019, which claims the benefit of priority under 35 U.S.C. § 119(e) of U.S. Provisional Patent Application No. 62/664,302 filed Apr. 30, 2018 entitled "POLYMERIC CORE-SHELL PARTICLES". The contents of the above applications are all incorporated by reference as if fully set forth herein in their entirety.

FIELD OF INVENTION

The present invention relates to the field of polymeric systems and their diagnostic use for e.g., cancer.

BACKGROUND OF THE INVENTION

Imaging techniques for early detection of the onset and progress of cancer are crucial for optimal therapeutic management. Positron Emission Tomography (PET) is the prominent functional imaging modality for identifying tumors in the clinic. However, false-positive identification of cancer using PET, or PET with computed tomography (CT), can reach high rates of 25-42%. PET is mostly used with the glucose analogue $^{18}$F-2-fluoro-2-deoxy-d-glucose (FDG), which exploits the increased glucose metabolic activity of cancer cells. FDG-PET has revolutionized the field of medical oncology, and is a powerful tool for cancer detection, staging and follow-up, especially when combined with a structural imaging modality such as CT or MRI.

However, a major shortcoming of this technology is the non-specificity for tumors. Although FDG measures the uptake of glucose, FDG cannot distinguish between cancer and inflammation. A number of biological events, such as an infection or inflammation, as well as tumors, result in increased glucose metabolic activity. For this reason, high rates of false positive findings are reported in FDG-PET imaging. False positive screening has severe economic consequences, entailing heavy expenditures on the healthcare systems, including unnecessary treatments, and waste of resources and labor force in vain.

Moreover, anti-cancer treatments such as surgery, chemotherapy and radiation therapy, tend to induce inflammation (not necessarily within the tumor region).

Since FDG-PET is inconclusive and does not discriminate between cancer recurrence and post-treatment inflammatory conditions it is crucial to develop a new methodology that enables metabolic-based cancer imaging, which can differentiate between cancer and metabolically active inflammatory processes.

Most blood vessels in tumors exhibit marginal blood flow and highly impaired lymphatic drainage, enabling retention of macromolecules in the tumor. In contrast, inflammation is characterized by increased blood flow and development of an expanded network of lymphatics. This enables visualizing cancer tissues and metastases even at an early stage of their development, and distinguishing these tissues from inflammation and from other tissues.

SUMMARY OF THE INVENTION

The present invention relates to the field of polymeric systems and their diagnostic use e.g., for cancer.

According to an aspect of the present invention there is provided a nanoparticle having a lipidic core, wherein the lipidic core is linked via one or more first polymeric linkers to one or more glucose molecules, and is further linked via one or more second polymeric linkers to one or more chelating agents, and wherein the glucose comprises 2-Deoxy-D-Glucose.

In some embodiments, a weight ratio of the glucose molecules to the nanoparticle is 1:20 to 1:80, respectively.

In some embodiments, a weight ratio of the chelating agents to the nanoparticle is 1:20 to 1:80, respectively.

In some embodiments, the first and second polymeric linkers comprises a polymer selected from the group consisting of: polylactic acid (PLA), poly lactic-co-glycolic acid (PLGA), polycaprolactone (PCL), polyethylene glycol (PEG), bovine serum albumin (BSA), human serum albumin (HSA), gelatin, and any derivative or combination thereof. In some embodiments, the polymer comprises polyethylene glycol (PEG), or a derivative thereof.

In some embodiments, the nanoparticle is in the form of liposome, the liposome comprising phospholipid.

In some embodiments, the phospholipid comprises one or more compounds selected from the group consisting of: 1,2-distearoyl-sn-glycero-3-phosphoethanolamine (DSPE), 2-Dimyristoyl-sn-glycero-3-phosphorylcholine (DMPC), Dipalmitoylphosphatidylcholine (DPPC), L-α-phosphatidylcholine, hydrogenated soy (HSPC), 1,2-dioleoyl-3-trimethylammonium-propane (DOTAP), Sphingomyelin, L-α-phosphatidylserine (Soy).

In some embodiments, the one or more glucose molecules and/or the one or more chelating agents are linked to the first polymeric linker via the carboxy moiety.

In some embodiments, the one or more glucose molecules and/or the one or more chelating agents are linked to the second polymeric linker via the amine moiety.

In some embodiments, the chelating agent has attached thereto an imaging agent.

In some embodiments, the imaging agent is selected from the group consisting of: radioactive label, fluorophore, chromophore, metal, and any combination thereof.

In some embodiments, the radioactive label is selected from the group consisting of: technetium-99m, iodine-123, iodine-131, rhenium-186, copper-64, rhenium-188, gallium-67, yttrium-90, lutetium-177, and any combination thereof.

In some embodiments, the chelating agent is a metal chelator. In some embodiments, the metal chelator is selected from the group consisting of: 1-(1,3-carboxy-propyl)-4,7,10-(carboxymethyl)-1,4,7,10-tetraazacyclododecane (DOTAGA), 1-(1,2-carboxyethyl)-4,7,10-(carboxymethyl)-1,4,7,10-tetraazacyclododecane (DOTASA) or 1,4,7,10-tetraazaacyclo-dodecane-1,4,7,10-tetra-acetic acid (DOTA), or any combination thereof. In some embodiments, the chelator is DOTA.

According to another aspect of the present invention, there is provided a composition comprising a plurality of the nanoparticles in an embodiment thereof.

In some embodiments, a median size of the nanoparticles is in the range of 60 nm to 180 nm.

In some embodiments, a size of at least 95% of the plurality of nanoparticles varies within a range of less than |±20%|.

According to another aspect of the present invention, there is provided a pharmaceutical formulation comprising or diagnostic effective amount of the disclosed composition, or particles, in an embodiment thereof, and a pharmaceutically acceptable carrier.

In some embodiments, the pharmaceutical formulation further comprises a diagnostic agent.

In some embodiments, the therapeutic agent is an anti-cancer therapeutic agent.

According to another aspect of the present invention, there is provided a method of imaging a tumor in a mammal, the method comprising administering to the subject the disclosed nanoparticle in an embodiment thereof, and performing a diagnostic imaging technique, thereby obtaining an image of the tumor.

In some embodiments, the administering is performed by an intravenous injection.

In some embodiments, the diagnostic imaging technique is selected from the group consisting: computed X-ray tomography (CT), ultrasound (US), positron emission tomography (PET), magnetic resonance imaging (MRI), and any combination thereof.

According to another aspect of the present invention, there is provided a method of differentiating between of an inflammatory process and a malignant disease in a site in a mammal, the method comprising administering to the mammal the nanoparticle in an embodiment thereof, performing a diagnostic imaging technique to obtain an image of the site, thereby differentiating between an inflammatory process and a malignant disease.

According to another aspect of the present invention, there is provided a kit comprising the nanoparticle in an embodiment thereof.

According to another aspect of the present invention, there is provided a kit for preparing a loaded liposome, the kit comprising (i) a first container comprising a particle comprising a core and a shell, wherein the core comprises a lipid, the shell comprises one or more polymeric linkers, and (ii) a second container comprising a one or more agents selected from glucose and a chelating agent. In some embodiments, the kit further comprises (iii) instructions for combining the contents of the first and second containers to prepare the loaded liposome.

In some embodiments, the kit further comprises an imaging agent.

In some embodiments, the kit further comprises instructions for combining the imaging agent and the particle.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE DRAWINGS

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description together with the drawings makes apparent to those skilled in the art how embodiments of the invention may be practiced.

In the drawings.

DETAILED DESCRIPTION OF THE INVENTION

Figure 1A:
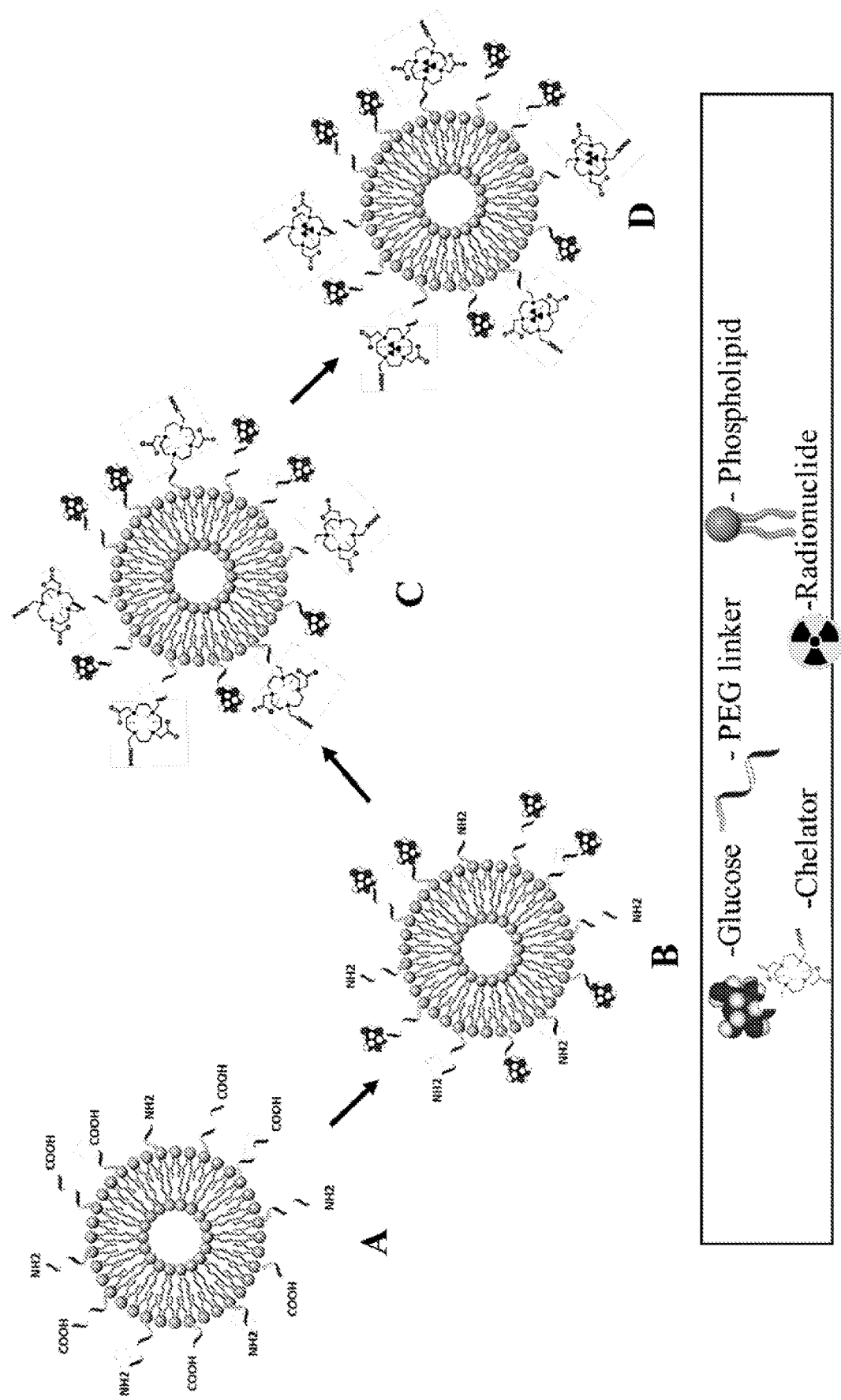
FIGS. 1A-1B are schematic representations of the preparation steps of the radio-labeled gluco-liposomes; liposomes were coated with PEG-COOH and PEG-NH$_2$ (A), followed by glucosamine coating (B), a metal chelator (1,4,7,10-tetraazacyclo-dodecane-1,4,7,10-tetra-acetic acid; DOTA) is conjugated to the available amine group (C), which may be complexed with radioactive Cu isotope (D); the final glucose-functionalized liposome is conjugated to the chelator-radioactive isotope of copper ($^{64}$Cu) complex (PEG; polyethylene glycol) (FIG. 1A); liposomes coated with PEG-COOH (A), followed by activation of the carboxyl groups (B), coating with glucosamine and a metal chelator (C), which may be complexed with radioactive tracer ions (D) (FIG. 1B)
Figure 1B:
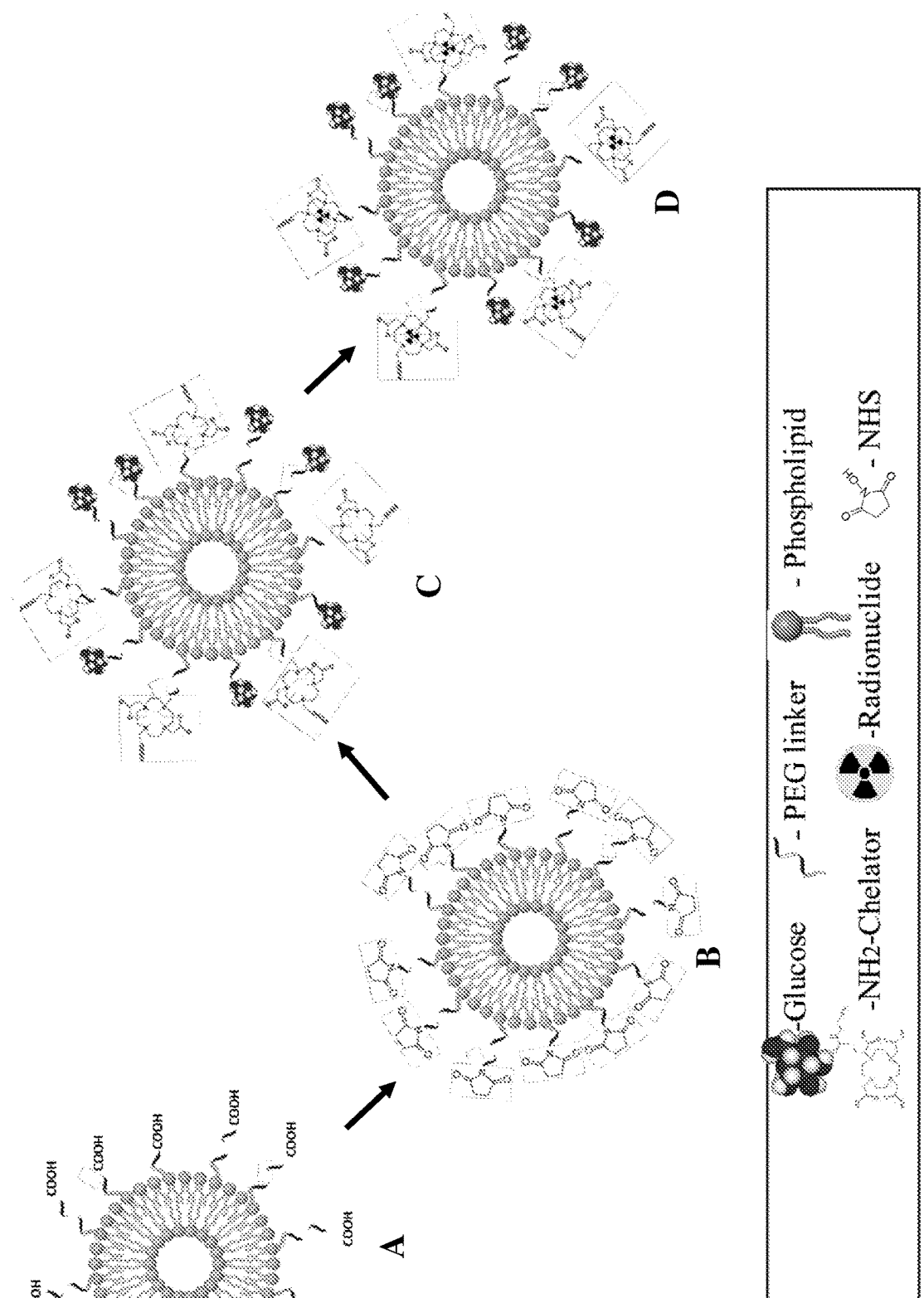

The present invention, in some embodiments, provides a composition comprising at least one lipid or polymeric particle, having polymeric linkers.

Before explaining at least one embodiment of the invention in detail, it is to be understood that the invention is not necessarily limited in its application to the details set forth in the following description or exemplified by the Examples. The invention is capable of other embodiments or of being practiced or carried out in various ways.

The Composition

The present invention, in some embodiments thereof, relates to therapy and diagnosis (theranostic) and more particularly, but not exclusively, to lipid and polymeric systems in which a glucose, a labeling moiety (e.g., a radioactive tracer) and/or a therapeutically active agent are attached to the polymeric system, and to uses thereof in diagnostic and theranostic applications.

In some embodiments, the polymeric system is in the form of particle (e.g., nano-size particle) as described herein.

In some embodiments, the nanoparticle is in the form of a core-shell structure e.g., having a lipid-based core (also referred to as: "lipidic core"), and at least one linking moiety.

In some embodiments, the term "core-shell structure" generally refers to a solid material, wherein the solid material is a particulate material, and wherein individual particle(s) is characterized by containing at least two different types of materials which may be distinguished from one another by their shape, by their diameter, by their composition, by their structure and/or by their placement within the particle, wherein one or more materials of a certain type are contained in the interior portion of the particles. The interior portion is designated by the term "core" or "matrix" or "inner matrix".

In some embodiments, one or more materials of a certain type which may be distinguished from the one or more materials contained in the interior portion are contained in the outer portion of the particles. The outer portion comprising the surface is designated by the terms "shell" or "coating layer" or "encapsulation layer".

In some embodiments, the core comprises the lipid, e.g., in the form of a liposome.

In some embodiments, there is provided a nanoparticle having a lipidic core, wherein the lipidic core is linked via one or more first polymeric linkers to one or more glucose molecules, and is further linked via one or more second polymeric linkers to one or more chelating agents.

In some embodiments, there is provided a nanoparticle having a lipidic core, wherein the nanoparticle is linked via one or more first polymeric linkers to one or more glucose molecules, and is further linked via one or more second polymeric linkers to one or more chelating agents.

Herein throughout, the phrase "linking moiety" is also referred to herein as "linker".

In some embodiments, the linker is a polymeric linker.

In some embodiments, the linker is attached to at least one surface of the core, i.e. to the shell.

In some embodiments, the first polymeric linker and the second polymeric linker are both anchored to, attached to, or comprise the same polymeric chain. In some embodiments, the first polymeric linker and the second polymeric linker are both anchored to, attached to, or comprise a different polymeric chain.

In some embodiments, the first linker comprises one or more agents selected from: glucose molecule, and a chelator as described herein. In some embodiments, the second linker comprises one or more agents selected from: glucose molecule, and a chelator as described herein.

One of skill in the art will appreciate that the order of the linkers may be altered in various embodiments and that the nomenclature "first polymeric linker" and "second polymeric linker" is used herein for ease of reference.

In some embodiments, the glucose comprises 2-Deoxy-D-Glucose.

In some embodiments, the term "lipid" refers to a hydrocarbon residue having e.g., 3-30 carbon atoms. In some embodiments, the term "lipid" refers to phospholipid. In some embodiments, the term "lipid" refers to glycerolipid.

The term "phospholipid" is used herein to collectively describe compounds that include a non-polar lipid group and a highly polar end phosphate group. One particular family of phospholipid compounds is the phosphoglycerides family of compounds. In some embodiments, the term "phospholipid" is used hereinthroughout to describe phosphoglycerides.

The term "phosphoglyceride" is therefore used herein to describe compounds having a glycerol backbone, one or more lipid moieties and one or more phosphate end group, which are attached to the glycerolic backbone.

In some embodiments, the polymeric linker comprises one or more moieties selected from —NH$_2$ (amine group), —COOH (carboxyl group).

Other exemplary linkers are selected from, without being limited thereto, thiol, thioalkoxy, thioaryloxy, hydroxy, and sulfonyl.

In some embodiments, the first or the second polymeric linkers are either natural or synthetic polymer.

As used herein, the term "polymer", or any grammatical derivative thereof describes an organic substance composed of a plurality of repeating structural units (monomeric units) covalently connected to one another.

In some embodiments, the first polymeric linker and the second polymeric linker, independently from each other, comprise a polymer selected from, without being limited thereto: polylactic acid (PLA), poly lactic-co-glycolic acid (PLGA), polycaprolactone (PCL), polyethylene glycol (PEG), bovine serum albumin (BSA), human serum albumin (HSA), gelatin, and any combination thereof.

In some embodiments, the first or the second polymeric linker comprise PEG. In some embodiments, the PEG is functionalized with NH$_2$ (referred to as "PEG-NH$_2$"). In some embodiments, the PEG is functionalized with COOH (referred to as "PEG-COOH"). In some embodiments, the PEG is functionalized with PEG-COOH and PEG-NH$_2$. In some embodiments, a molar ratio of PEG-NH$_2$ to PEG-COOH ratio is 1:9 to 1:1, e.g., 1:9, 1:8, 1:7, 1:6, 1:5, 1:4, 1:3, 1:2, or 1:1, respectively, including any value and range therebetween.

In some embodiments, "PEG" refers to a branched or linear condensation polymer of ethylene oxide and water, represented by the general formula H(OCH$_2$CH$_2$)$_n$OH wherein n is an integer having a value of at least 4. In some embodiments, n ranges from 4 to 50. In some embodiments, n ranges from 20 to 50. In some embodiments, n ranges from 40 to 50. In some embodiments, n is 40, 41, 42, 43, 44, 45, 46, 47, 48, 49, or 50, including any range therebetween.

In some embodiments, the molecular weight of the polymer is in the range of from 400 Da to 1500 Da. In some embodiments, the molecular weight of the polymer is in the range of from 200 Da to 2 kDa. In some embodiments, the molecular weight of the polymer is in the range of from 500 Da to 5 kDa. In some embodiments, the molecular weight of the polymer is in the range of from 200 Da to 5 kDa, 500 Da to 5 kDa, 700 Da to 5 kDa, 500 Da to 3 kDa, 500 Da to 2 kDa, 1 kDa to 5 kDa, 1.1 kDa to 5 kDa, 1.5 kDa to 5 kDa, 1 kDa to 2 kDa, 1.1 kDa to 2 kDa, or 1.5 kDa to 2 kDa, including any range therebetween.

In some embodiments, the polymer comprises linear chains. In some embodiments, polymer chains linked to the nanoparticle surface are able to create steric hindrance, resulting in a significant inhibition of protein adsorption and less recognition by macrophages.

As used herein, the term "weight average molecular weight" ($M_w$) generally refers to a molecular weight measurement that depends on the contributions of polymer molecules according to their sizes.

In some embodiments, the "PEG" has an approximate average molecular weight of about 1 kDa, about 2 kDa, about 3 kDa, about 4 kDa, about 5 kDa, about 6 kDa, about 7 kDa, about 8 kDa, about 9 kDa, or about 10 kDa, including any value and range therebetween.

As described herein, in some embodiments, the lipid-based system is in the form liposome or a micelle.

In some embodiments, the lipid (or liposome) comprises one or more lipids selected from, without being limited thereto: 1,2-Dimyristoyl-sn-glycero-3-phosphorylcholine (DMPC), Dipalmitoylphosphatidylcholine (DPPC) 1,2-Distearoyl-sn-glycero-3-phosphoethanolamine (DSPE), L-α-phosphatidylcholine, hydrogenated soy (HSPC), 1,2-dioleoyl-3-trimethylammonium-propane (DOTAP), Sphingomyelin, L-α-phosphatidylserine (Soy), or any combination thereof.

Ratios of the lipids may vary according to embodiments visualized by persons skilled in the art of liposome preparation.

The term "liposome" as used herein means a vesicle including one or more concentrically ordered lipid bilayer(s) encapsulating an aqueous phase, when in an aqueous environment. Formation of such vesicles requires the presence of "vesicle-forming lipids" which are defined herein as amphipathic lipids capable of either forming or being incorporated into a bilayer structure. The term includes lipids that are capable of forming a bilayer by themselves or when in combination with another lipid or lipids.

In some embodiments, the liposome is a PEGylated liposome. In some embodiments, the lipid is attached to a polymeric linker. In some embodiments, a portion of the lipids is attached to a polymeric linker. In some embodiments, 1% to 99%, 5% to 99%, 10% to 99%, 15% to 99%, 20% to 99%, 30% to 99%, 40% to 99%, 50% to 99%, 60% to 99%, 1% to 98%, 1% to 95%, 1% to 90%, 1% to 85%, 1% to 80%, 10% to 95%, 10% to 90%, 20% to 95%, 20% to 98%, or 20% to 90% of the lipids are attached to a polymeric linker.

In some embodiments, the polymeric linker is a PEG linker.

In some embodiments, the particle is attached to at least one chelating agent (also referred to as: "chelator"). In some embodiments, the polymeric linker is attached to at least one chelating agent.

In some embodiments, the particle is attached to at least one chelating agent via a polymeric linker. Embodiments of the polymeric linker are described herein.

In some embodiments, the particle is attached to at least one chelating agent via an amine or carboxyl moiety of the linker. In some embodiments, the polymeric linker is attached to at least one chelating agent via an amine or carboxyl moiety of the linker.

In one embodiment, the weight ratio of the particle (e.g., liposome) to chelating agent is 15:1 to 90:1, e.g., 15:1, 20:1, 25:1, 30:1, 35:1, 40:1, 45:1, 50:1, 55:1, 60:1, 75:1, 80:1, 85:1, or 90:1, including any value and range therebetween.

In one embodiment, the weight ratio of the particle (e.g., liposome) to glucose is 15:1 to 90:1, e.g., 15:1, 20:1, 25:1, 30:1, 35:1, 40:1, 45:1, 50:1, 55:1, 60:1, 75:1, 80:1, 85:1, or 90:1, including any value and range therebetween.

In one embodiment, the weight ratio of the particle (e.g., liposome) to glucose is 15:1 to 90:1, e.g., 15:1, 20:1, 25:1, 30:1, 35:1, 40:1, 45:1, 50:1, 55:1, 60:1, 75:1, 80:1, 85:1, or 90:1, including any value and range therebetween. In one embodiment, the weight ratio of the liposome to glucose is 15:1 to 90:1, e.g., 15:1, 20:1, 25:1, 30:1, 35:1, 40:1, 45:1, 50:1, 55:1, 60:1, 75:1, 80:1, 85:1, or 90:1, including any value and range therebetween.

In one embodiment, the weight ratio of glucose:particle (e.g., liposome):chelating agent is from about 1:20:1 to about 1:80:1, e.g., about 1:20:1, about 1:30:1, about 1:40:1, about 1:50:1, about 1:60:1, about 1:70:1, or about 1:80:1, including any value and range therebetween.

In some embodiments, the particle (or the polymeric system) is in the form of a nano-sized particle (also referred to as "nanoparticle").

Herein, the particle weight or the nanoparticle weight do not to include the glucose and the chelating agent.

In some embodiments, the chelating agent is a metal chelator.

In some embodiments, composition comprises a metal chelator selected from, without being limited thereto, 1-(1,3-carboxy-propyl)-4,7,10-(carboxymethyl)-1,4,7,10-tetraazacyclododecane (chelator DOTAGA), 1-(1,2-carboxyethyl)-4,7,10-(carboxymethyl)-1,4,7,10-tetraazacyclododecane (chelator DOTASA) or 1,4,7,10-tetraazaacyclo-dodecane-1,4,7,10-tetra-acetic acid (chelator DOTA), or any combination thereof. In exemplary embodiments, the chelator is DOTA.

In some embodiments, the lipid core is conjugated to glucose.

In some embodiments, the lipid core is conjugated to the glucose via the first polyeric linker.

In some embodiments, the first polymeric linker (e.g., PEG) is conjugated to the glucose via a carboxyl moiety of the polymeric linker.

In some embodiments, by "conjugated to" it is meant to refer to being coupled to. In some embodiments, by "conjugated to" it is meant to refer to being linked to, e.g., covalently linked.

In some embodiments, "by linked", it is meant to refer to being bound via a covalent bond, or via an electrostatic bond.

In some embodiments, the glucose is 2-deoxy-D-glucose (2-DG).

In some embodiments, the glucose is 2-amino-2-deoxy-D-glucose (2-glucosamine).

In some embodiments, the term "conjugated system" refers to a system of atoms covalently bonded with alternating single and multiple bonds.

The terms "2-deoxy-D-glucose" and "2-DG" are used interchangeably herein to refer to a glucose molecule in which the 2-hydroxyl group is replaced by hydrogen, so that it cannot undergo further glycolysis and derivative and analogue thereof. Typically, 2-deoxy-D-glucose is taken up by glucose transporters of the cell, therefore, cells with higher glucose uptake, for example tumor cells, have also a higher uptake of 2-DG.

As used herein, the term "analogue" refers to a chemical compound with a structure and function similar to that of a reference compound but differing from it in respect to a particular component, functional group, atom, etc.

As used herein, a 2-DG analog is any D-glucose analog other than 2-DG that does not have a hydroxyl group at the 2' position of the glucose ring. An analog of glucose or 2-DG can have a fluorine in place of a hydrogen at any position on the glucose ring; thus, 2-fluoro-2-deoxy-D-glucose (2-FDG) and 2-difluoro-2-deoxy-D-glucose are 2-DG analogs. An analog of 2-DG can have an amino group in place of a hydroxyl group at any position on the glucose ring other than the 6' position; thus, 2-amino-2-deoxy-D-glucose (2-glucosamine) and 2-amino-2-deoxy-D-galactose (2-galactosamine) are 2-DG analogs. Other illustrative 2-DG analogs include 2-F-mannose, 2-mannosamine, 2-deoxygalactose, 2-F-deoxygalactose, and di, tri, and other oligosaccharides that contain one or more of the preceding or following 2-DG analogs. Analogs are commercially available and/or can be synthesized by one of skill in the art using routine techniques with reference to the scientific literature.

In some embodiments, the chelator is configured to attach one or more agents (e.g., imaging agent) selected from: radioactive label, fluorophore, chromophore, metal, and any combination thereof.

In one embodiment, the weight ratio of the particle (e.g., liposome) to the imaging agent is in the range of from 100:1 to 500:1, e.g., 100:1, 200:1, 300:1, 400:1, or 500:1, including any value and range therebetween.

In some embodiments, the fluorophore comprises nitrobenzoxadiazole (NBD). In some embodiments, the imaging agent is nitrobenzoxadiazole (NBD) fluorescent dye. In some embodiments, the liposomes were labeled with nitrobenzoxadiazole (NBD) fluorescent dye.

In some embodiments, by "metal" it is also meant to encompass metal ion.

In some embodiments, the label or the metal is a radioactive label.

In some embodiments, the radioactive label is selected from, but is not limited to: technetium-99m, iodine-123, iodine-131, rhenium-186, rhenium-188, gallium-67, gallium-68, yttrium-90, lutetium-177, copper-64, and any combination thereof.

In some embodiments, the polymeric system (or the particle) is characterized by a desired median size, e.g., diameter.

In some embodiments, the term "diameter" encompasses a size of at least one dimension, e.g., length. In some embodiments, the "diameter" refers to a median size of a polymeric system. In some embodiments, the term "diameter" refers to "hydrodynamic diameter". In some embodiments, the term "diameter" refers to the core of the polymeric system.

In some embodiments, the diameter ratio of the (core+shell)/core is 10:8, 10:9, or approaches 1:1, including any value therebetween.

In some embodiments, "hydrodynamic diameter" refers to a size determination for a macromolecule or colloid particle in solution (e.g., aqueous solution) using any technique known in the art, e.g., dynamic light scattering (DLS).

In some embodiments, the hydrodynamic diameter is 100 to 200 nm. In some embodiments, the hydrodynamic diameter is 140 nm, 150 nm, 160 nm, 170 nm, 180 nm, 190 nm, or 200 nm, including any value and range therebetween.

In some embodiments, a plurality of the polymeric systems is characterized by a diameter that varies within less than ±20%, less than ±15%, less than ±10%, or less than ±5%.

In some embodiments, the polymeric system is characterized by a negative Zeta- ($\zeta$-) potential.

In some embodiments, the polymeric system is characterized by a $\zeta$-potential of −4 to −8 mV, e.g., −4, −4.5, −5, −5.5, −6, −6.5, −7, −7.5, or −8 mV, including any value and range therebetween.

Method of Diagnosis

In some embodiments, the disclosed nanoparticles (or the composition comprising the same in an embodiment thereof) is internalized by and accumulates in tumor cells/cancer cells in vivo.

In some embodiments, and without being bound by any particular theory, the nanoparticles are accumulated in the site (e.g., the tumor or the tissue) by an enhanced permeation and retention (EPR) effect.

In some embodiments, the composition is internalized by and accumulates in tumor cells/cancer cells in vitro. In some embodiments, the internalization and accumulation of the composition in vivo is specific to cancer cells or significantly higher in cancer cells than non-cancer cells. In some embodiments, accumulation of the composition in tumor cells/cancer cell allows imaging of these cells. In some embodiments, the composition accumulates in vivo in cells of a tumor rather than in cells of an inflamed tissue, therefore allows differentiating between cancer and inflammatory processes.

In some embodiments, the composition accumulates and it is retained by and in tumor cells/cancer cells in vitro. In some embodiments, the composition accumulates and it is retained by and in tumor cells/cancer cells in vivo.

In some embodiments, the composition has a higher accumulation in cells of a tumor than in cells of an inflamed tissue. In some embodiments, the composition has an accumulation in cells of a tumor at least 1 fold, at least 2 fold, at least 3 fold, at least 4 fold, at least 5 fold, at least 6 fold, at least 7 fold, at least 8 fold, at least 9 fold, at least 10 fold, at least 20 fold, at least 50 fold, or at least 100 fold higher than accumulation at in cells of an inflamed tissue In some embodiments, the composition of the invention comprises one or more imaging agents, as described herein.

In some embodiments, the nanoparticles or the composition of the invention allow to enhance image contrast during diagnostic imaging. The term "diagnostic medical imaging", or simply "medical imaging" or "diagnostic imaging" refers to a method of graphically or pictorially investigating an animal or human body for the purposes of studying the body's anatomy or physiology or an abnormality thereof. Typical methods of medical imaging which are contemplated by the present invention include, among others, computed X-ray tomography (CT), ultrasound (US), positron emission tomography (PET), magnetic resonance imaging (MRI), and optical imaging.

As used herein, the terms "tumor cells" and "cancer cells" are used interchangeably to refer to cells characterized by unregulated cell growth.

The term "tumor" as used herein encompasses both primary and metastasized solid tumors and carcinomas of any tissue in a subject, including, but not limited to breast; colon; rectum; lung; oropharynx; hypopharynx; esophagus; stomach; pancreas; liver; gallbladder; bile ducts; small intestine; urinary tract including kidney, bladder and urothelium; female genital tract including cervix, uterus, ovaries (e.g., choriocarcinoma and gestational trophoblastic disease); male genital tract including prostate, seminal vesicles, testes and germ cell tumors; endocrine glands including thyroid, adrenal, and pituitary; skin (e.g., hemangiomas and melanomas), bone or soft tissues; blood vessels (e.g., Kaposi's sarcoma); brain, nerves, eyes, and meninges (e.g., astrocytomas, gliomas, glioblastomas, retinoblastomas, neuromas, neuroblastomas, Schwannomas and meningiomas). The term "tumor" also encompasses solid tumors arising from hematopoietic malignancies such as leukemia, including chloromas, plasmacytomas, plaques and tumors of mycosis fungoids and cutaneous T-cell lymphoma/leukemia, and lymphomas including both Hodgkin's and non-Hodgkin's lymphomas. The term "tumor" also encompasses radio resistant and/or chemo resistant tumors, including, but not limited to radio resistant and/or chemo resistant variants of any of the tumor listed above.

As used herein, the term "inflamed tissue" includes tissues that have elevated inflammatory response cells infiltrates. Inflamed tissue may be characterized by one or more of the following: (1) dilation of capillaries to increase blood flow to the affected area; (2) changes in the microvasculature structure, leading to the escape of inflammatory response cells from circulation; and/or (3) inflammatory response cells migrating from the capillaries and accumulating at the site of inflammation.

As used herein the term "in vivo" refers to any process/event that occurs within a living subject. As used herein the term "in vitro" refers to any process/event that occurs outside a living subject in an artificial environment, such as in cell culture. In some embodiment, in vitro refers to cell lines grown in cell culture. In some embodiment, in vitro refers to tumor cells grown in cell culture.

In some embodiments, the tumor/cancer cells are glucose transporter overexpressing cells (e.g., GLUT1 overexpression).

In some embodiments, the accumulation of the composition in tumor cells is significantly higher than that of a similar composition in which the 2-deoxy-D-glucose is substituted by other glucose molecules.

"Other glucose molecules", as used herein, include any derivative of glucose in which the hydroxyl group at position 2 was not replaced, such as for a non-limiting example: L-glucose, D-glucose, 1-deoxy-D-glucose, 3-deoxy-D-glucose, 4-deoxy-D-glucose, 6-deoxy-D-glucose or other derivatives thereof.

A "similar composition", as used herein, differ from the compositions of the invention only by substitution of a component as described (e.g., substitution of 2-deoxy-D-glucose with other glucose molecules, substitution of polymer or derivatives thereof).

In some embodiments, the imaging agent comprises a magnetic particle. Any magnetic particle suitable for use for imaging by MRI may be used in the composition and methods of the present disclosure. The magnetic particle may be formed, at least in part, from any material affected by a magnetic field. Examples of suitable materials include, but are not limited to: magnetite, hematite, ferrites, and materials comprising one or more of iron, cobalt, manganese, nickel, chromium, gadolinium, neodymium, dysprosium, samarium, erbium, iron carbide, iron, or a combination thereof. In some embodiments, the particle is a metal particle. Examples of suitable metals include, but are not limited to: gold, silver, platinum, palladium, cobalt, iron, copper, tin, tantalum, vanadium, molybdenum, tungsten, osmium, iridium, rhenium, hafnium, thallium, lead, bismuth, gadolinium, dysprosium, holmium, and uranium, or a combination thereof.

The present invention also provides a method of the prophylaxis, diagnosis or treatment of cancers as well as the inhibition of tumor growth and metastasis, wherein the polymeric systems or the compositions are characterized by low antigenicity, high activity and long half-life.

In some embodiments, the method comprises the steps of: administering to a subject the composition of the invention, wherein the composition penetrates to and accumulates in tumor cells of the subject; and scanning the subject or a portion thereof, thereby imaging the tumor cells. In some embodiments, the composition is utilized for imaging tumors overexpressing GLUT-1.

In some embodiments, the scanning step is performed 0.5 to 24 hours post the administering step. In some embodiments, the scanning step is performed 0.5 to 12 hours post the administering step. In some embodiments, the scanning step is performed 1 to 12 hours post the administering step. In some embodiments, the scanning step is performed 1 to 6 hours post the administering step. In some embodiments, the scanning step is performed within 24 hours from the administering step. In some embodiments, the scanning step is performed within 12 hours from the administering step. In some embodiments, the scanning step is performed within 6 hours from the administering step.

In some embodiments, a portion of a subject include any area of interest of a subject's body.

The tumors that are suitable to be treated or diagnosed with the method include, but not limited to, lung cancer, hepatoma, gastric cancer, esophageal cancer, bone cancer, pancreatic cancer, lymphoma, colon cancer, breast cancer, prostate cancer, oral cancer, nasopharyngeal carcinoma, uterine cervix cancer, leukemia, malignant melanoma, sarcoma, renal cancer, biliary cancer, etc.

The present invention also provides the administration routes of the aforementioned polymeric system. The administration routes include, but not limited to, intravenous injection, intravenous drip, venous canal administration, arterial canal administration, intramuscular injection, intraperitoneal injection, oral administration, inhalation administration, subcutaneous administration, dermal administration, rectal administration, vaginal administration, nasal mucosa administration, oral mucosa administration, ocular administration, or other administration routes.

Methods for Treatment

As described hereinabove, in some embodiments, the present invention provides a method of imaging a tumor in a mammal suffering from or suspected to suffer from cancer by administering the composition of the invention. In one embodiment, the composition is administered by an intravenous (IV) injection. In some embodiments, the imaging is performed by using a diagnostic imaging technique selected from but not limited to: CT, US, PET, and MRI.

In some embodiments, the invention provides a method for treating or suppressing cancer. In some embodiments, the method comprises the steps of: administering to a subject the composition of the invention, wherein the composition reaches to and accumulates on/in tumor or metastases of the subject; and directing ionizing irradiation (e.g., x-ray) to the composition to obtain locally enhanced radiation therapy within the tumor or metastases.

In one embodiment, the present invention provides a method for treating, prognosticating or determining the suitability for treatment of a subject suffering from cancer by administration of the composition together with therapeutic active agent(s).

In one embodiment, the present invention provides a method of treating cancer with the composition by administering the composition of the invention together with a therapeutic active agent (also referred to as "drug") to a subject in need thereof. In one embodiment, the drug is activated within the tumor cells. In some embodiments, the subject is a human subject.

In some embodiments, upon administration of the disclosed composition, the method further comprises a step of directing an ionizing irradiation to the composition, thereby obtaining locally enhanced radiation therapy within the tumor cells.

As used herein, the term "drug" refers to pharmacologically active molecules that are used to diagnose, treat, or prevent diseases or pathological conditions in a physiological system (e.g., a subject, or in vivo, in vitro, or ex vivo cells, tissues, and organs). Drugs act by altering the physiology of a living organism, tissue, cell, or in vitro system to which the drug has been administered. In some embodiments, the drug is anti-cancer therapeutic agent/chemotherapeutic agent. It is intended that the terms "anti-cancer therapeutic agent" and "chemotherapeutic agent" encompass anti-hyperproliferative and antineoplastic compounds as well as other biologically therapeutic compounds.

In some embodiments, the composition comprises the polymeric system in an embodiment thereof and a pharmaceutically acceptable excipient. In another embodiment, the composition comprises the polymeric system in an embodiment thereof and a buffer.

As used hereinthroughout, the term "subject" refers to any animal (e.g., a mammal), including, but not limited to, humans, non-human primates, rodents, and the like (e.g., which is to be the recipient of a particular treatment, or from whom cancer stem cells are harvested). Typically, the terms "subject" and "patient" are used interchangeably, unless indicated otherwise herein.

In some embodiments, the subject is a human subject. In some embodiments, the subject is a human subject at risk of being afflicted with cancer. In some embodiments, the subject is diagnosed with a cancer. In some embodiments, the cancer is a cancer associated with GLUT-1 overexpression.

As used herein, the term "subject at risk of being afflicted with cancer" refers to a subject that presents one or more signs or symptoms indicative of a cancer (e.g., a noticeable lump or mass) or is being screened for a cancer (e.g., during a routine physical). A subject at risk of being afflicted with cancer may also have one or more risk factors. A subject at risk of being afflicted with cancer encompasses an individual that has not been previously tested for cancer. However, a "subject at risk of being afflicted with cancer" also encompasses an individual who has received a preliminary diagnosis (e.g., a CT scan showing a mass) but for whom a confirmatory test (e.g., biopsy and/or histology) has not been performed or for whom the stage of cancer is not known. The term further includes a subject who once had cancer (e.g., an individual in remission).

A "subject at risk of being afflicted with cancer" may be diagnosed with cancer or alternatively found not to have cancer.

As used herein, the term "subject diagnosed with a cancer" refers to a subject who has been tested and found to have cancerous cells. The cancer may be diagnosed using any suitable method, including but not limited to, biopsy, X-ray, blood test, and the diagnostic methods of the present invention. A "preliminary diagnosis" is one based only on visual (e.g., CT scan or the presence of a lump) and antigen tests.

In some embodiments, the subject is a human subject afflicted with cancer. In some embodiments, the subject is afflicted with cancer and the imaging method is used for determining the stage of the cancer. In some embodiments, the subject afflicted with cancer was treated with anti-cancer drug, and the imaging method is used for follow up of the treatment.

In some embodiments, the method further comprises the step of analyzing the imaging data. In some embodiments, treatment decision may be not to administer a therapy when a tumor was not imaged. In some embodiments, the analysis of the imaging data is used for deciding on a route of treatment adequate to the patient. In some embodiments, deciding on a route of treatment adequate to the patient depends on tumor size and location, on the stage of the disease, as well as on the health state of the patient. In some embodiments, the route of treatment includes one or more protocols of treatment selected from the group consisting of: surgery, radiosurgery, chemotherapy, a treatment comprising administration of cytostatic(s), cytotoxic(s), a targeted therapy, a vaccine, radionuclides, immune-radionuclides, and any other biological or inorganic product intended to treat cancer. In some embodiments, a treatment is administered subsequent to the imaging. In some embodiments, a treatment is administered to the subject in real time, while imaging the tumor. For a non-limiting example, a radiation treatment may be administered to the location of the tumor while imaging the tumor. In another non-limiting example, imaging the tumor may be helpful prior and post a surgery to remove the tumor.

In some embodiments, where the composition further comprises a drug, the composition serves both for diagnostic imaging and as a therapeutic agent. In some embodiments, imaging and treating the tumor is performed simultaneously. In some embodiments, the drug may be activated in the tumor subsequent to imaging such as by using ultrasonic waves to release the drug from the composition. In some embodiments, the drug remains attached to the polymeric system of the composition and is used to treat tumor cells.

In some embodiments, the polymeric system of the composition are radiation absorbing particles.

As used herein, the term "radiation absorbing particles" refers to particles which absorb electromagnetic radiation (including as non-limiting examples infrared, near-infrared (NIR) and radio-frequency (RF) radiation) and convert the absorbed energy to released heat which can be used to create localized hyperthermia. In some embodiments, the composition is used for thermal ablation of tumor cells in which the composition accumulates, without causing damage to surrounding normal tissues or substantial toxicity to the subject.

According to some embodiments, the invention provides a method for diagnosing cancer. The method may comprise the steps of: administering to a subject the composition of the invention, wherein the composition penetrates to and accumulates on/in tumor or metastases of the subject; scanning the subject or a portion thereof, thereby imaging the tumor.

According to some embodiments, the invention provides a kit comprising the disclosed compositions. In some embodiments, the disclosed compositions may be provided in a kit, together with instructions for use.

In some embodiments, the kit comprises one container comprising a pre-conjugated liposomes with glucose and a chelating agent. In some embodiments, the kit comprises one container comprising a nanoparticle having a lipidic core, wherein the nanoparticle is linked via one or more first polymeric linkers to one or more glucose molecules, and is further linked via one or more second polymeric linkers to one or more chelating agents.

In some embodiments, the kit comprises a first container including polymeric system or liposome of a desired composition as disclosed herein, and instructions for mixing the contents of the first and second containers at a desired ratio as described above to provide a liposomal composition containing the chelating agent and the glucose (i.e., to provide a loaded liposome).

In some embodiments, the kit comprises a first container comprising a particle comprising a core and a shell, wherein the core comprises a lipid, the shell comprises one or more polymeric linkers, and a second container comprising a one or more agents selected from glucose and a chelating agent. In some embodiments, the kit comprises a first container comprising a particle comprising a core and a shell, wherein the core comprises a lipid, the shell comprises one or more polymeric linkers, a second container comprising one or more glucose, and a third container comprising one or more chelating agents as disclosed herein.

In some embodiments, the kit comprises an imaging agent as disclosed herein. In some embodiments, an imaging agent is obtained separately. In some embodiments, the kit comprises instructions for combining the imaging agent and the particle.

The kit may further include the instructions for administering the composition to a subject (e.g., indication, dosage, methods etc.). In yet another example the kit may include instructions of to apply the compositions and methods of the invention to imaging systems e.g., CT, US, PET, and MRI.

In some embodiments, the invention provides kits useful for methods disclosed herein. A kit may include a container having a sterile reservoir that houses any composition disclosed herein.

In some embodiments, the content of the kit is packaged, as described below, to allow for storage of the components until they are needed.

In some embodiments, some or all components of the kit may be packaged in suitable packaging to maintain sterility.

In some embodiments, the components are stored in separate containers within the main kit containment element e.g., box or analogous structure, may or may not be an airtight container, e.g., to further preserve the sterility of some or all of the components of the kit.

In some embodiments, the dosage amount of the one or more components provided in a kit may be sufficient for a single application or for multiple applications.

In those embodiments, the kit may have multiple dosage amounts of the components packaged in a single container, e.g., a single tube, bottle, vial, Eppendorf and the like.

In some embodiments, the kit comprises multiple dosage amounts of the components individually packaged. In some embodiments, multiple dosage amounts of the one or more components may be packed in single separate containers.

In some embodiments, the kit contains instructions for preparing compositions as described elsewhere herein, and for practicing the methods of the invention.

In some embodiments, the instructions are recorded on a suitable recording medium or substrate. For example, the instructions may be printed on a substrate, such as paper or plastic, etc.

In some embodiments, the instructions are present in the kit as a package insert, in the labeling of the container of the kit or components thereof (i.e., associated with the packaging or sub-packaging) etc. In other embodiments, the instructions are present as an electronic storage data file. In other embodiments, the actual instructions are not present in the kit, but means for obtaining the instructions from a remote source, e.g. via the internet, are provided. An example of this embodiment is a kit that includes a web address where the instructions can be viewed and/or from which the instructions can be downloaded. As with the instructions, this means for obtaining the instructions is recorded on a suitable substrate.

According to some embodiments, the shelf life and/or the pot life of the components are long enough to allow them to be manufactured, stored and/or shipped to a user in a ready-for-use form, requiring no further process or preparation.

Pharmaceutical Composition

The present invention also contemplates pharmaceutical compositions for human medical use, which comprise the nanoparticle or composition of the invention with optionally therapeutic active agent(s), for the diagnosis of cancer.

In some embodiments, the pharmaceutical formulation comprises a diagnostic effective amount of one or more pharmaceutically acceptable carriers.

As used herein, a "pharmaceutically acceptable formulation" may include any of a number of carriers such as solvents, dispersion media, coatings, surfactants, antioxidants, preservatives (e.g., antibacterial agents, antifungal agents), isotonic agents, absorption delaying agents, salts, preservatives, drugs, drug stabilizers, gels, binders, excipients, disintegration agents, lubricants, sweetening agents, flavoring agents, dyes, such like materials and combinations thereof, as would be known to one of ordinary skill in the art (Remington's, 1990). Pharmaceutical compositions containing the presently described polymeric systems as the active ingredient can be prepared according to conventional pharmaceutical compounding techniques. See, for example, Remington's Pharmaceutical Sciences, 18th Ed., Mack Publishing Co., Easton, Pa. (1990). See also, Remington: The Science and Practice of Pharmacy, 21st Ed., Lippincott Williams & Wilkins, Philadelphia, Pa. (2005).

A pharmaceutical composition may comprise different types of carriers depending on whether it is to be administered in solid, liquid or aerosol form, and whether it need to be sterile for such routes of administration as injection.

Also contemplated are methods using compositions that are sterile solutions for injection or for application by any other route. A person of ordinary skill in the art would be familiar with techniques for generating sterile solutions for injection or application by any other route. Sterile injectable solutions are prepared by incorporating the active compounds in the required amount in an appropriate solvent with various other ingredients familiar to a person of skill in the art.

Suitable formulations can include, but are not limited to, injectable formulations including for example, solutions, emulsions, and suspensions. The compositions contemplated herein may take the form of solutions, suspensions, emulsions, combinations thereof, or any other pharmaceutical acceptable formulation as would commonly be known in the art.

In some embodiments, the carrier is a solvent. For a non-limiting example, the composition may be disposed in the solvent. Such a solvent includes any suitable solvent known in the art such as water, saline, phosphate-buffered saline.

The formulation of the composition may vary depending upon the route of administration. For parenteral administration in an aqueous solution, for example, the solution should be suitably buffered if necessary and the liquid diluent first rendered isotonic with sufficient saline or glucose. Sterile aqueous media which can be employed will be known to those of skill in the art in light of the present disclosure.

Supplementary active ingredients can also be incorporated into the compositions. For human administration, preparations should meet sterility and general safety and purity standards as required by FDA Office of Biologics standards. Administration may be by any known route.

The pharmaceutical composition may comprise various antioxidants to retard oxidation of one or more component.

Additionally, the prevention of the action of microorganisms can be brought about by preservatives such as various antibacterial and antifungal agents, including but not limited to parabens (e.g., methylparabens, propylparabens), chlorobutanol, phenol, sorbic acid, thimerosal or combinations thereof. The pharmaceutical composition must be stable under the conditions of manufacture and storage, and preserved against the contaminating action of microorganisms, such as bacteria and fungi. It will be appreciated that exotoxin contamination should be kept minimally at a safe level, for example, less than 0.5 ng/mg protein.

In embodiments where the pharmaceutical composition is in a liquid form, a carrier can be a solvent or dispersion medium comprising but not limited to, water, ethanol, polyol (e.g., glycerol, propylene glycol, liquid polyethylene glycol, etc.), lipids (e.g., triglycerides, vegetable oils, liposomes) and combinations thereof. In many cases, it will be preferable to include isotonic agents, such as, for example, sugars, sodium chloride or combinations thereof.

In other embodiments, a nasal solutions or sprays, aerosols or inhalants may be used. Nasal solutions are usually aqueous solutions designed to be administered to the nasal passages in drops or sprays.

Solid pharmaceutical compositions for oral administration are also contemplated. In these embodiments, the solid composition may comprise, for example, solutions, suspensions, emulsions, tablets, pills, capsules (e.g., hard or soft shelled gelatin capsules), sustained release formulations, buccal compositions, troches, elixirs, suspensions, syrups, wafers, or combinations thereof. Oral compositions may be incorporated directly with the food of the diet. Preferred carriers for oral administration comprise inert diluents, edible carriers or combinations thereof. In other aspects, the oral pharmaceutical composition may be prepared as a syrup or elixir. Additional formulations which are suitable for other modes of administration include suppositories. Suppositories are solid dosage forms of various weights and shapes for insertion into the rectum, vagina or urethra.

Sterile injectable solutions may be prepared by incorporating the active compounds in the required amount in the appropriate solvent with various other ingredients enumerated above. The liquid medium should be suitably buffered if necessary and the liquid diluent first rendered isotonic prior to injection with sufficient saline or glucose.

Upon formulation, solutions will be administered in a manner compatible with the dosage formulation and in such amount as is effective.

The pharmaceutical composition may be administered to the subject using any method known to those of ordinary skill in the art. The mode of administration may vary based on the application. For example, the mode of administration may vary depending on the particular cell, tissue, organ, portion of the body, or subject to be imaged. For example, the composition may be administered intravenously, intracerebrally, intracranially, intrathecally, into the substantia nigra or the region of the substantia nigra, intradermally, intraarterially, intraperitoneally, intralesionally, intratracheally, intranasally, topically, intramuscularly, intraperitoneally, subcutaneously, orally, topically, locally, inhalation (e.g., aerosol inhalation), injection, infusion, continuous infusion, localized perfusion bathing target cells directly, via a catheter, via a lavage, in crèmes, in lipid compositions (e.g., liposomes), or by other method or any combination of the forgoing as would be known to one of ordinary skill in the art (Remington's, 1990).

In particular embodiments, the pharmaceutical composition is administered to a subject using a drug delivery device. Any drug delivery device is contemplated for use in delivering the polymeric system of the instant invention to a subject.

Definitions

The term "carboxy" or "carboxylate" describes a —C(=O)—OR' group, where R' comprises hydrogen, alkyl, cycloalkyl, alkenyl, aryl, heteroaryl (bonded through a ring carbon) or heteroalicyclic (bonded through a ring carbon) as defined herein.

The term "carbonyl" describes a —C(=O)—R' group, where R' is as defined hereinabove.

The above-terms also encompass thio-derivatives thereof (thiocarboxy and thiocarbonyl).

The term "amine" as used herein refers to a functional group comprising at least one NR'R" group, wherein R' and R" are independently selected from H and alkyl and includes, for example, a directly attached amine, an alkyl amine or an aromatic amine.

General

As used herein the term "about" refers to ±10%.

The terms "comprises", "comprising", "includes", "including", "having" and their conjugates mean "including but not limited to". The term "consisting of" means "including and limited to". The term "consisting essentially of" means that the composition, method or structure may include additional ingredients, steps and/or parts, but only if the additional ingredients, steps and/or parts do not materially alter the basic and novel characteristics of the claimed composition, method or structure.

The word "exemplary" is used herein to mean "serving as an example, instance or illustration". Any embodiment described as "exemplary" is not necessarily to be construed as preferred or advantageous over other embodiments and/or to exclude the incorporation of features from other embodiments.

The word "optionally" is used herein to mean "is provided in some embodiments and not provided in other embodiments". Any particular embodiment of the invention may include a plurality of "optional" features unless such features conflict.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

As used herein, the term "treating" includes abrogating, substantially inhibiting, slowing or reversing the progression of a condition, substantially ameliorating clinical or aesthetical symptoms of a condition or substantially preventing the appearance of clinical or aesthetical symptoms of a condition.

In those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

EXAMPLES

Reference is now made to the following examples which, together with the above descriptions, illustrate the invention in a non-limiting fashion.

Example 1

Synthesis, Conjugation and Characterization

Materials and Methods

PEGylated liposomes were synthesized based on the well-known filter-extrusion method. 1,2-Distearoyl-sn-glycero-3-phosphoethanolamine-N-[methoxy (polyethylene glycol) (DSPE-PEG)-COOH and DSPE-PEG-NH$_2$ were used for amine and carboxyl functionalization. Organic phospholipid solution was mixed with the aqueous solution, and the liposomes were downsized by step-wise extrusion, using the LiposoFast-Basic instrument with polycarbonate membranes. Glucosamine coating was achieved by EDC/NHS reaction (glucosamine with distearoyl-sn-glycero-3-phosphoethanolamine (DSPE)-PEG-COOH). The liposomal membrane was than labeled with 1,4,7,10-tetraazacyclododecane-1,4,7,10-tetraacetic acid (DOTA), which further complexed with $Cu^{2+}$ ions in order to simulate the radioactive tracer while enabling quantification of the nanoparticles uptake into cells (using ICP). Excess $Cu^{2+}$ ions were removed from the liposomes solution by dialysis.

Characterisation of the liposomes was conducted using dynamic light scattering and zeta potential measurements. In addition, $Cu^{2+}$ concentration in the final liposomes solution was measured using inductively coupled plasma (ICP).

Preparation of Liposomes Coated with 5% Glucose and 5% Chelating Agent:

PEGylated-liposomes were synthesized based on the filter-extrusion method-compressed gas was used to pressurize the sample through a polycarbonate membrane.

The extruder was preheated to 65° C. using a water bath.

Hydro Soy PC (HSPC), 1,2-distearoyl-sn-glycero-3-phosphoethanolamine-N-[carboxy(polyethylene glycol)-2000] (DSPE-PEG-COOH) and Cholesterol were weighted and dissolved in absolute EtOH at 70° C. at the desired molar ratios—in this procedure: 60:10:30. Final lipid concentration—44 mM. EtOH volume—10% of the desired final liposomes solution volume.

Calculating the Lipid Amount:

$$\text{Final solution volume}[L] \cdot \text{Total lipid concentration}\left[\frac{\text{mole}}{L}\right] \cdot \text{Molar Ratio} \cdot Mw\left[\frac{\text{gr}}{\text{mole}}\right] = X[\text{gr}]$$

The organic phospholipid solution was rapidly mixed with aqueous PBS×1 solution (PBS volume—90% of the desired final liposomes solution volume) and vortex.

The liposome solution was downsized by step-wise extrusion, using polycarbonate membranes—400 nm, 200 nm and 100 nm.

Liposomes coating was performed using a two-step EDC/Sulfo NHS covalent coupling procedure.

The carboxyl groups were activated with water-soluble 1-ethyl-3-[3-dimethylaminopropyl] carbodiimide (EDC). To prevent rapid hydrolysis of the active intermediate, N-hydroxysulfosuccinimide (Sulfo-NHS) was added to the reaction to form a more stable Sulfo-NHS ester intermediate. Number of EDC and sulfo-NHS moles required—5 times the number of COOH moles on liposomes surface. The reaction was placed at RT for 3 hrs under constant stirring. The solution PH was kept between 4.7-7.2. Excess EDC and NHS reagents was discarded by washing the liposomes solution using PD-10 desalting columns twice.

Glucosamine and chelating agent were added at ratio 1:1. Number of glucosamine and chelating agent moles required—2 times the number of COOH moles on the liposomes surface.

Excess of glucosamine and chelating agent were discarded by washing the liposomes solution using PD-10 desalting columns twice.

The radioactive tracer ions were added to the solution, and stirred at 50° C. for 1 hour.

Excess of radioactive tracer was discarded by washing the liposomes solution using PD-10 desalting column.

Results

The results showed that the liposomes solution was monodispersed with a mean hydrodynamic diameter of ±160 nm, no significant change in particle size was observed during the coating process.

Zeta potential results showed a slightly negative charge on the liposomes surface.

Figures 2A, 2B:
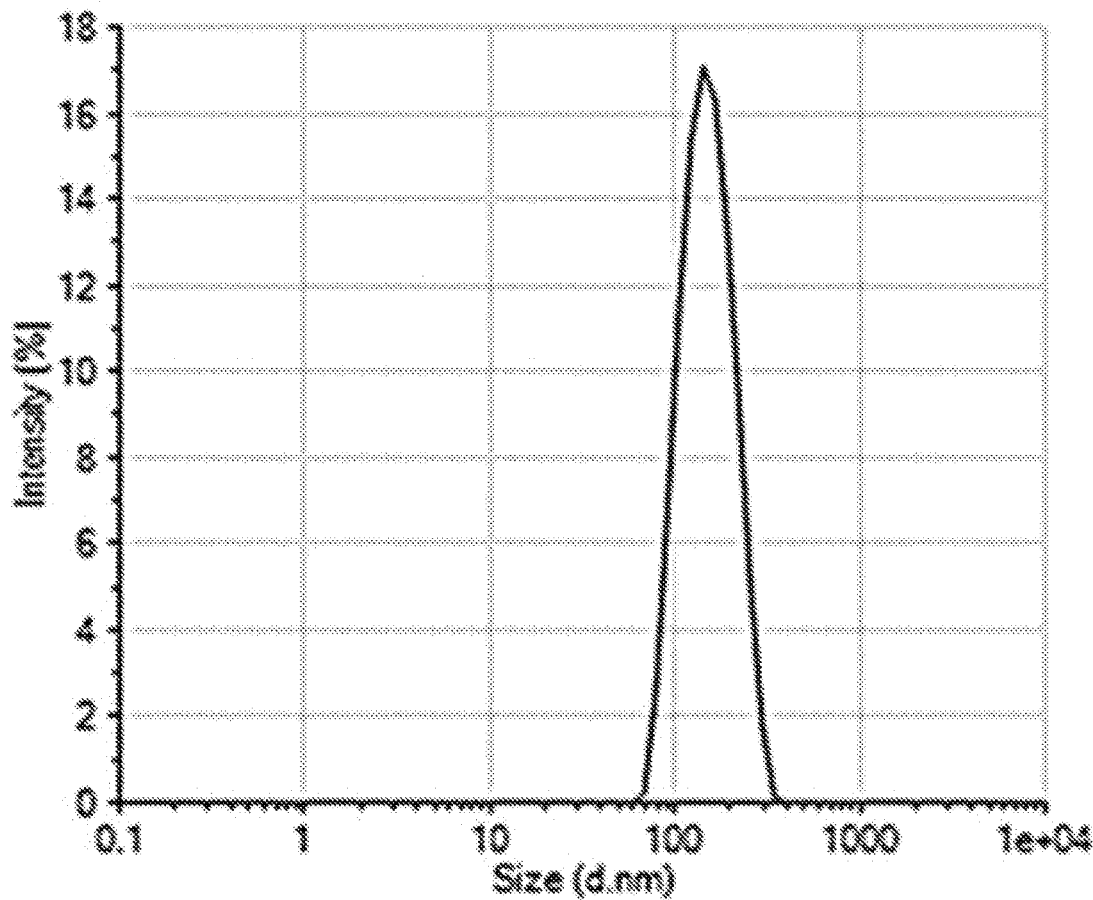
FIGS. 2A-2B present characterization of Cu-labeled liposomes: a graph showing size distributions obtained by dynamic light scattering (DLS) (FIG. 2A), and a table showing the mean hydrodynamic size and zeta potential of glucose-coated Cu-labeled liposomes, measured by DLS and zeta potential analyzer after each conjugation level (FIG. 2B)

According to ICP measurements, $Cu^{2+}$ concentration in the liposomes solution was 32.5 µg/ml. Based on this results, $Cu^{2+}$ ions amount was calculated to be ~$5·10^3$ $Cu^{2+}$ molecules per liposome (see FIGS. 2A-B).

Figure 3A:
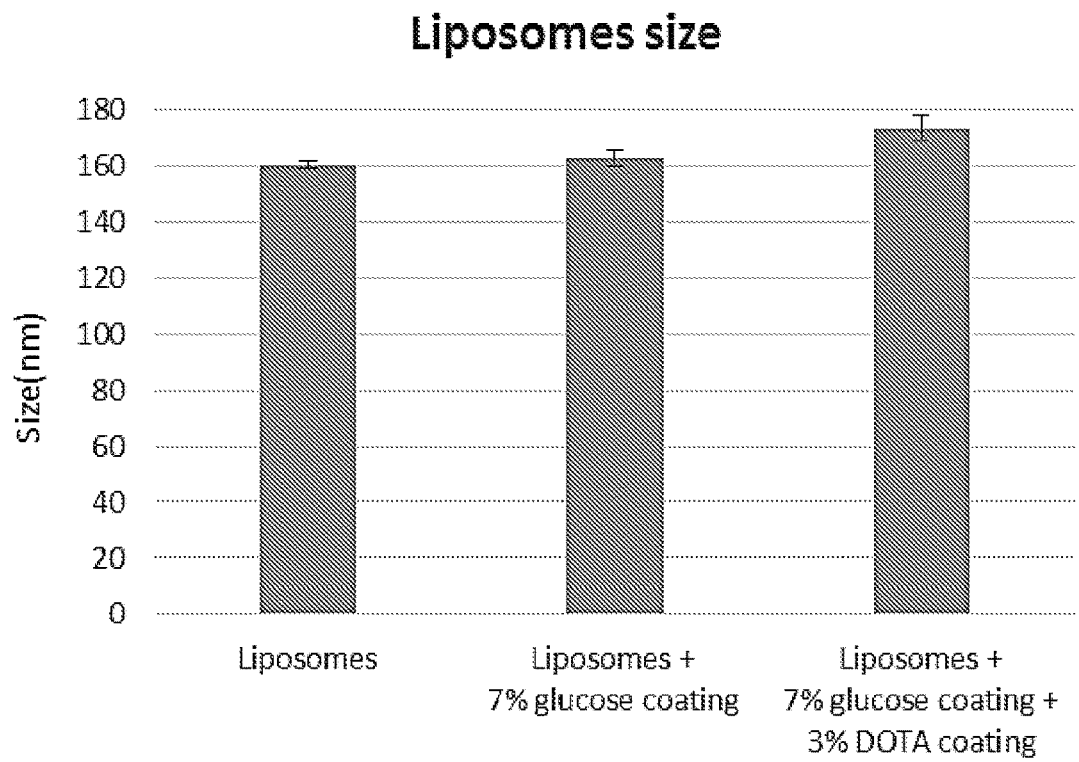
FIGS. 3A-3B present the characterization of glucose coated liposomes Cu-labeled with non-radioactive copper ion: a graph showing the size of liposomes following each conjugation step (FIG. 3A), and a graph showing the zeta potential measurements of the liposomes following each conjugation level (FIG. 3B)
Figure 3B:
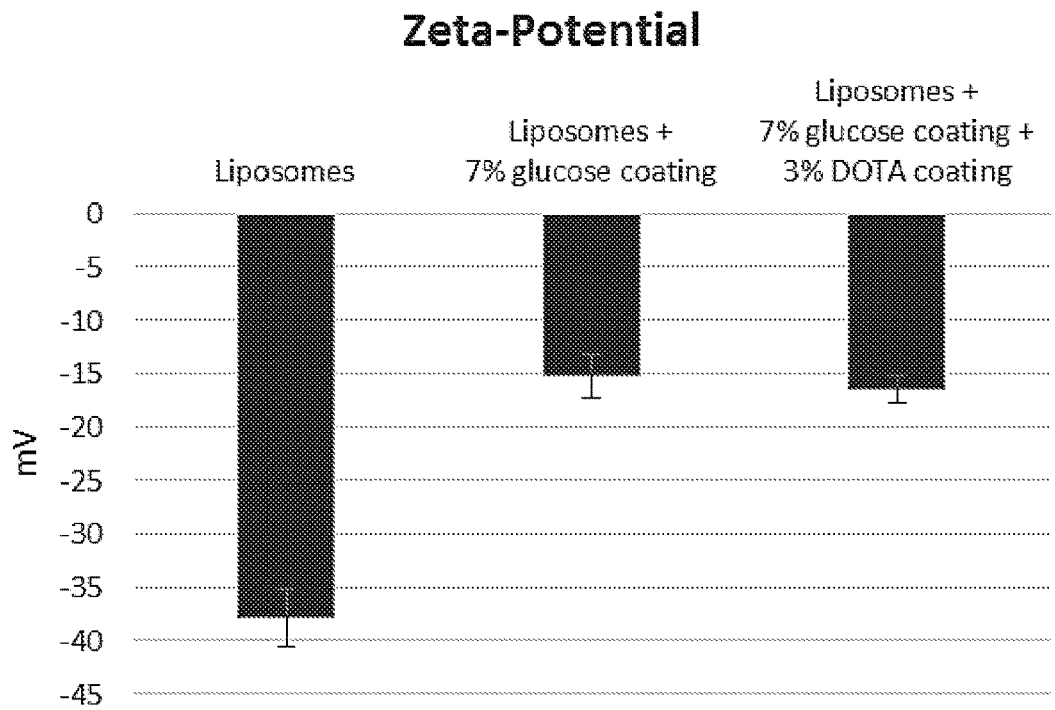

FIGS. 3A-B present the characterization of glucose coated liposomes Cu-labeled with non-radioactive copper ion: a graph showing the size of liposomes following each conjugation step (FIG. 3A), and a graph showing the zeta potential measurements of the liposomes following each conjugation level (FIG. 3B).

In-vitro investigation of the liposome uptake into cancer cells: Uptake of the $Cu^{2+}$-labeled gluco-liposomes was quantitatively investigated by incubating them with human lung cancer cells (A549) for 20 min, followed by quantification of $Cu^{2+}$ amount using ICP.

In order to verify the metabolic role in the liposomes uptake, the effect of glucose transporter-1 (GLUT1) was investigated using Cytochalasin B (a well-known GLUT1 inhibitor). Prior to incubation with liposomes, cells were incubated with Cytochalasin B for 2 hs.

Figure 4:
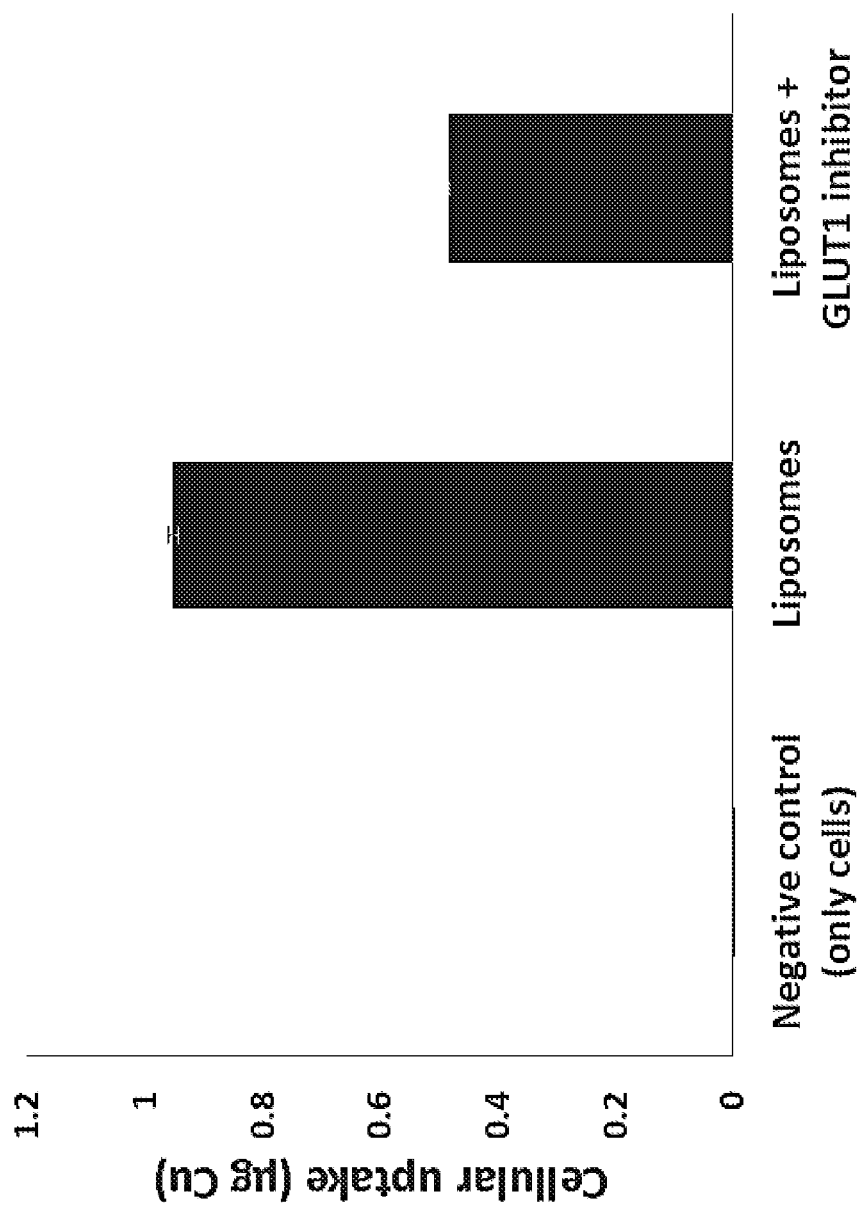
FIG. 4 presents a bar graph showing cellular uptake of Cu-labeled gluco-liposomes, measured by inductively coupled plasma (ICP) analysis, after 20 min incubation with human lung cancer cell line (A549), with or without GLUT1 inhibitor.

As a negative control, $Cu^{2+}$ amount in A549 cells without liposomes was measured. A significant reduction in the gluco-liposomes uptake was observed for cells that were pre-incubated with Cytochalasin B in comparison to cells that were only incubated with gluco-liposomes (see FIG. 4).

In vitro investigation of the nanoparticle accumulation and internalization into different types of cancer cells: The liposomes were labeled with nitrobenzoxadiazole (NBD) fluorescent dye by adding a pre-labeled phosphatidylcholine to the liposomes composition (16:0-12:0 NBD-phosphatidylcholine (1% molar ratio)). Liposomes uptake was examined in seven different cell lines: A431 head and neck squamous cell carcinoma, 4T1 breast adenocarcinoma, A549 non-small-cell lung carcinoma, PC3 prostate carcinoma, B16 melanoma (murine), LNCaP prostate adenocarcinoma and 3T3 fibroblasts (non-cancerous). The first five are known for high glucose transporter 1 (GLUT-1) expression, while the latter two are known for low GLUT1 expression. Each cell line was incubated (2 hrs) either with glucose-conjugated liposomes or with liposomes without glucose. Liposome uptake was measured by average fluorescence intensity.

Figure 5A:
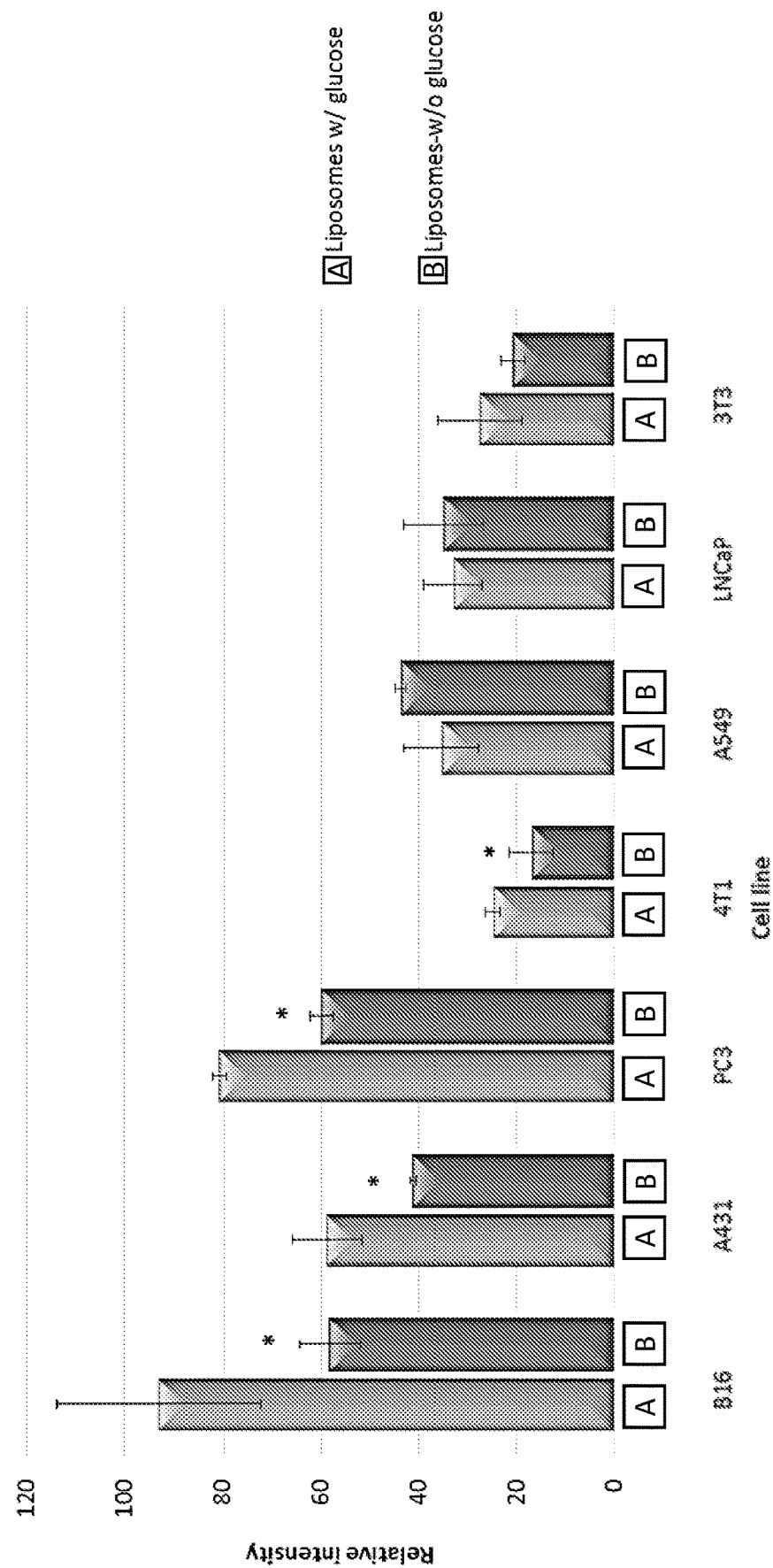
FIGS. 5A-5C present a bar graph showing the cellular uptake and accumulation of fluorescent liposomes into different types of cancer cells, with and without glucose labeling (FIG. 5A), representative images of B16 cells (FIG. 5B) and LNCaP cells (FIG. 5C), incubated with NBD-labeled liposomes; top: bright-field image of the cells, bottom: NBD-fluorescent images of the cells; DIC fluorescence microscope (fully motorized Nikon TE2000E), images acquired with a Retiga 2000R imager and the microscope and camera were controlled using Nikon NIS elements software. w/:with; w/o:without.
Figure 5B:
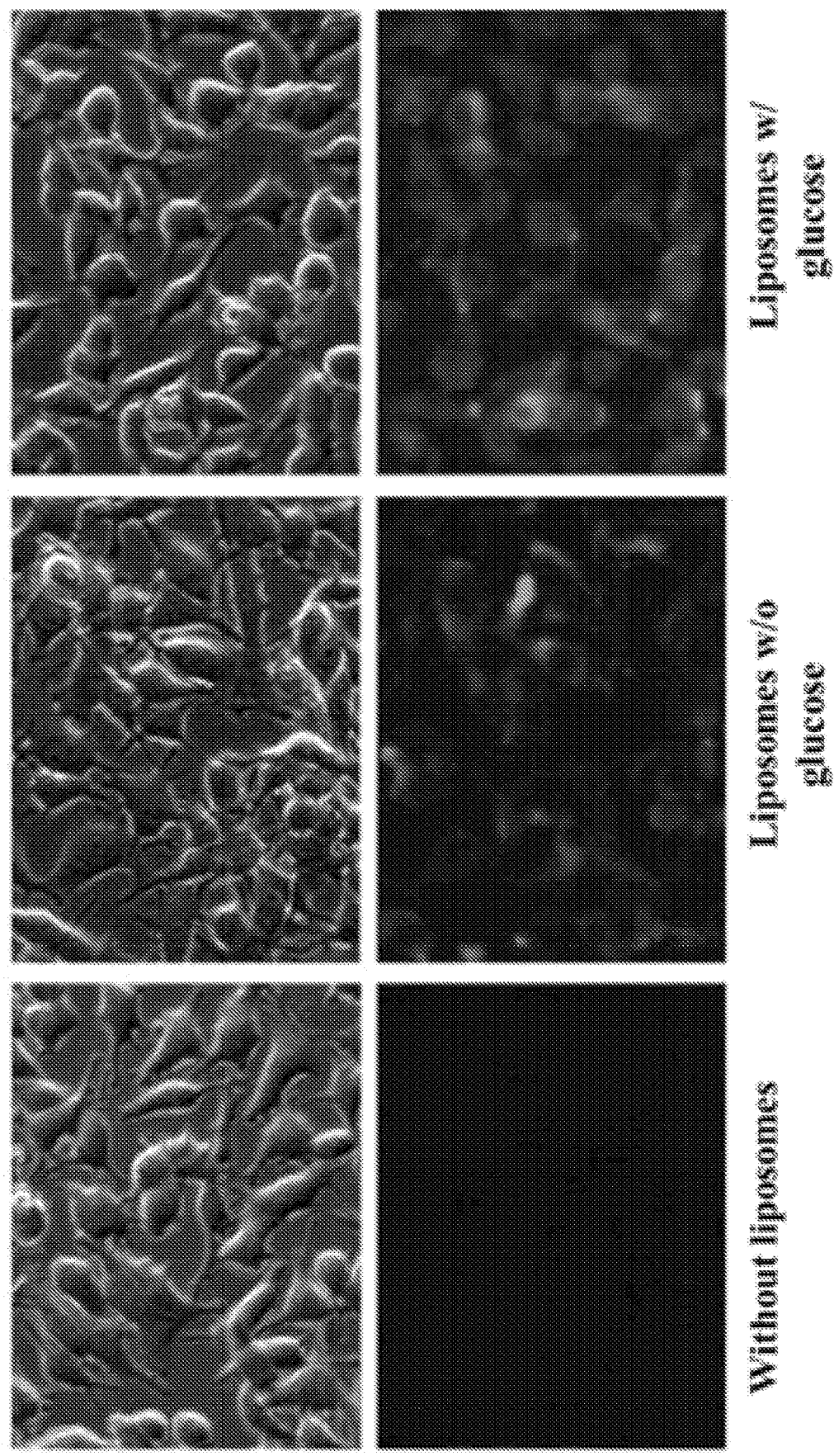
Figure 5C:
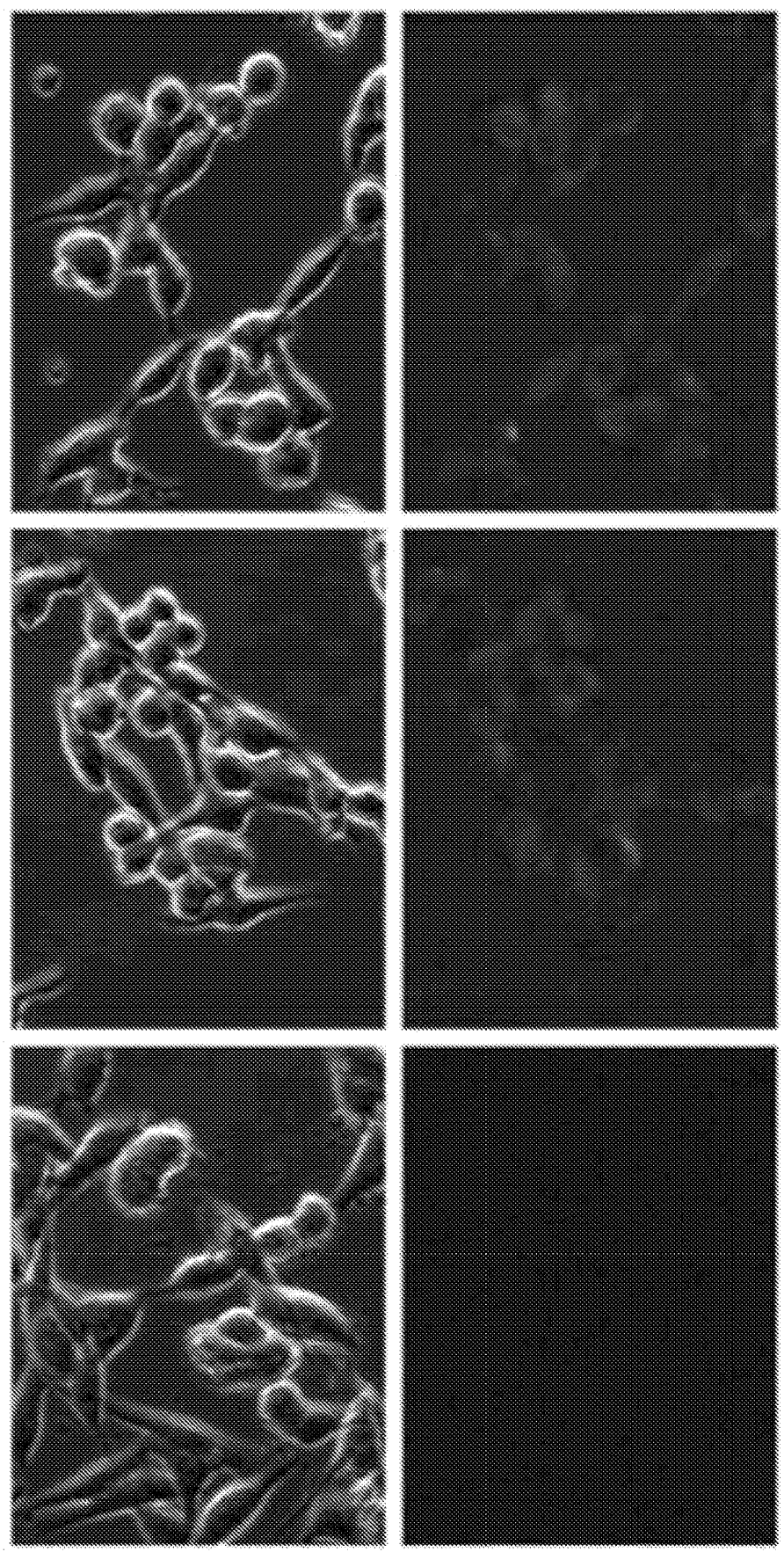

Cell lines known for their high GLUT-1 expression showed significantly higher uptake of glucose-coated liposomes as compared to non-coated liposomes. However, cells with low GLUT-1 expression showed similar uptake of glucose-coated and non-coated liposomes, likely due to the passive entry of liposomes into cells (see FIGS. 5A-C).

Figures 6A, 6B, 6C:
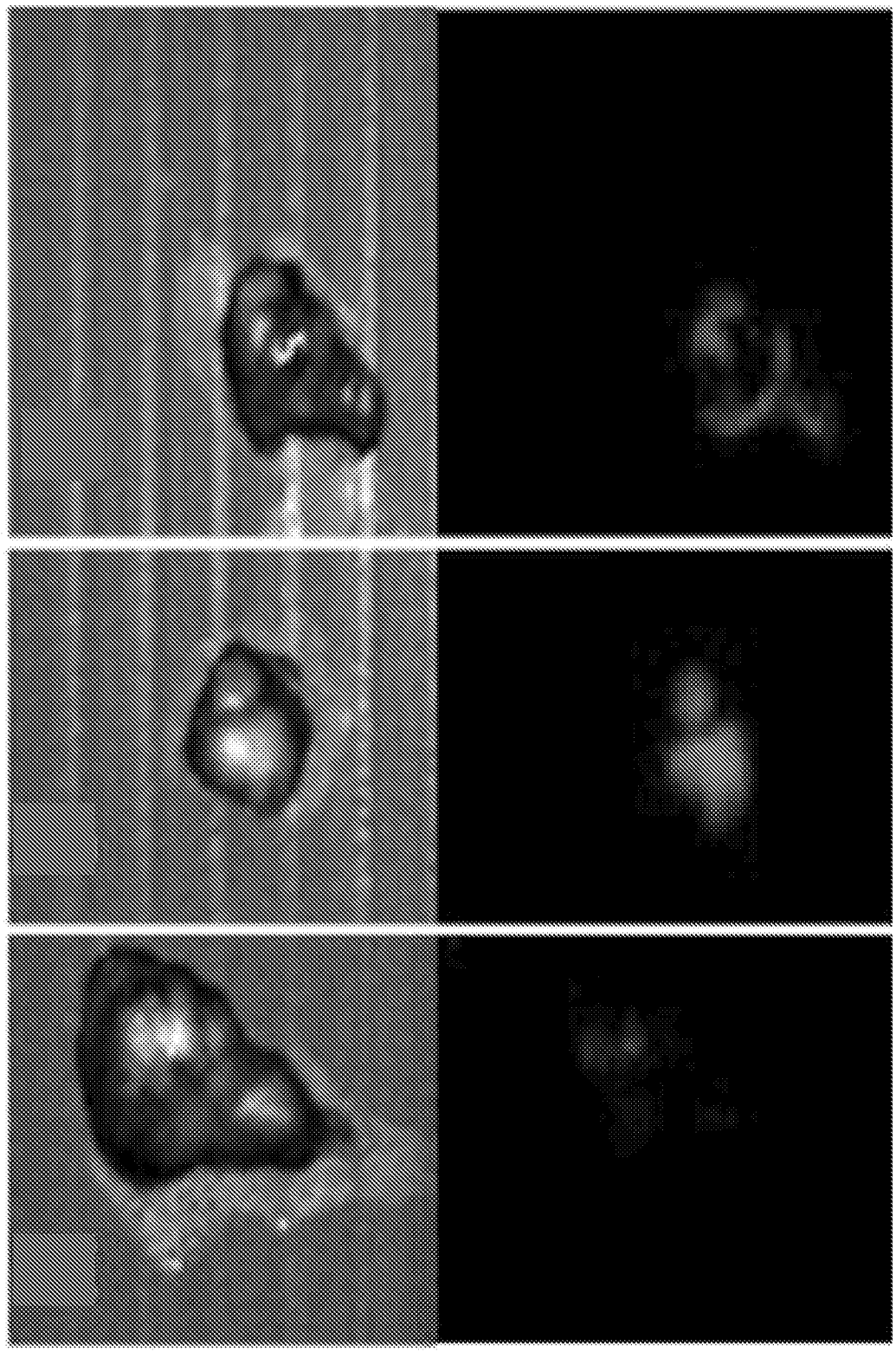
FIGS. 6A-6C present images of an Ex-vivo verification of NBD-labeled liposomes uptake into Melanoma (skin cancer) model: liposome accumulation in control tumor, mice which did not receive nanoparticle administration (FIG. 6A); tumor of mice treated with glucose coated liposomes (FIG. 6B); and tumor of mice treated with uncoated liposomes (FIG. 6C); top: tumor imaged with bright-field function of Maestro imaging; bottom: tumor imaged with fluorescence Maestro imaging.

FIGS. 6A-C present Ex-vivo verification of NBD-labeled liposomes uptake into Melanoma (skin cancer) model. Uptake was examined using a Maestro™ in vivo fluorescence imaging device.

Figure 7A:
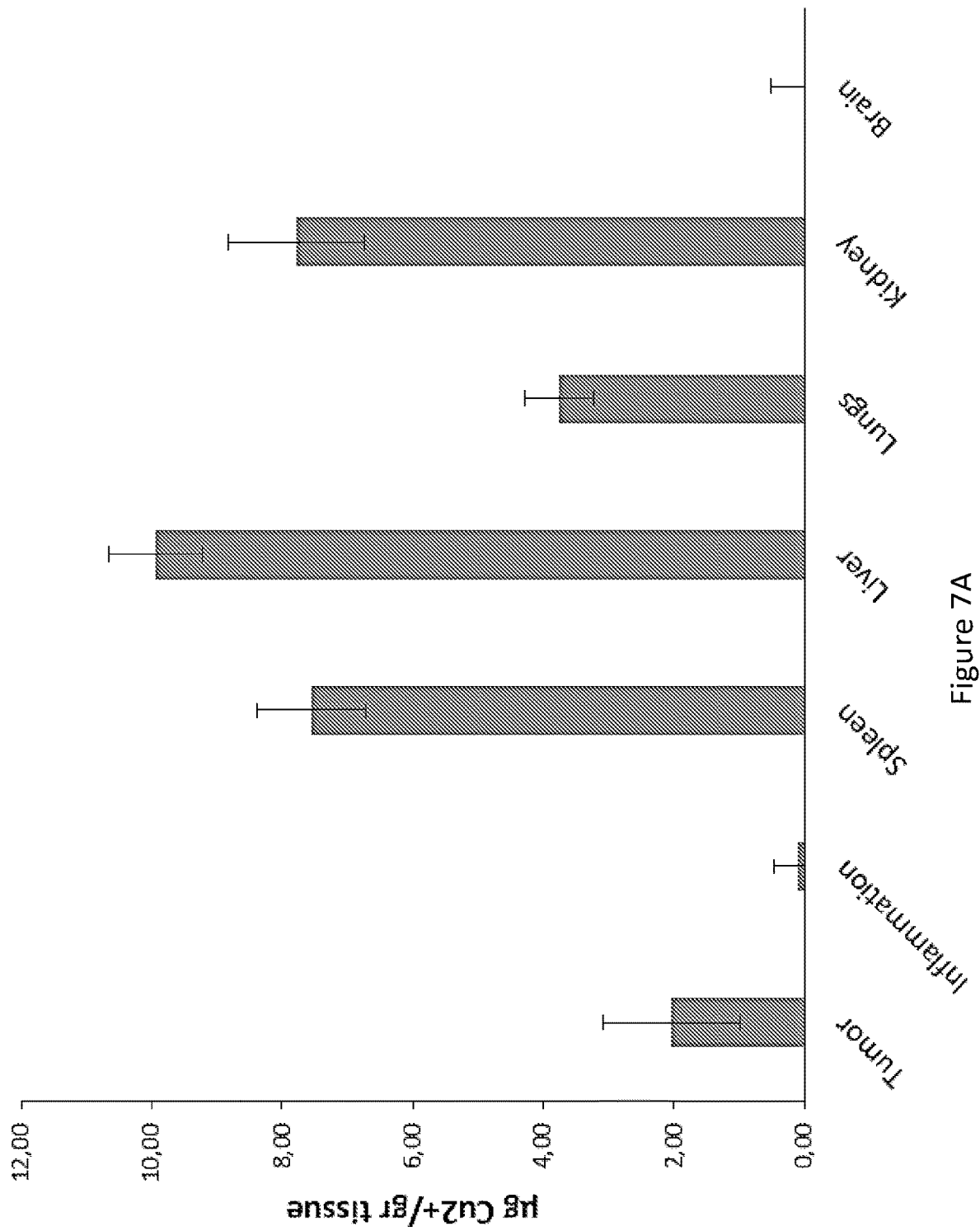
FIGS. 7A-7B present bar graphs showing the biodistribution of gluco-liposomes Cu-labeled with a non-radioactive copper ion (Cu): distribution in mice organs (FIG. 7A) and differentiation between cancer and inflammation (FIG. 7B); (*$p<0.05$ tumor vs. inflammation; n=3-5; values normalized to control $Cu^{+2}$ levels in organs of saline-injected mice); Infla.=inflammation region.
Figure 7B:
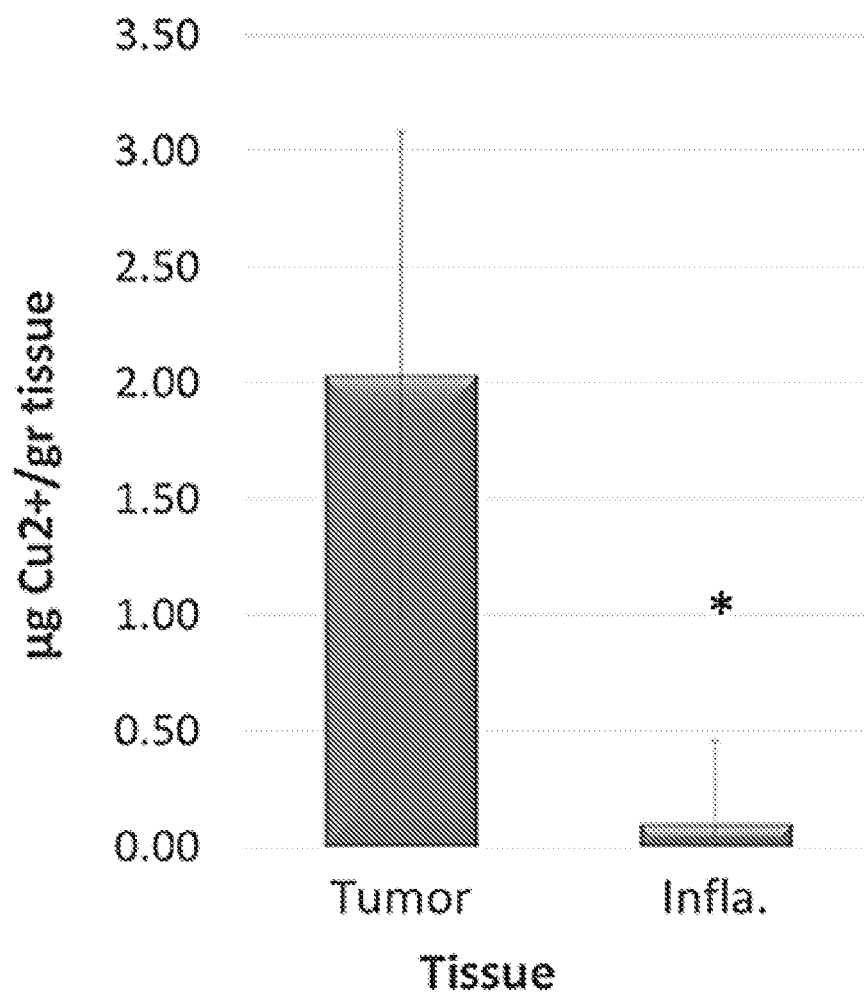

FIGS. 7A-B present bar graphs showing the biodistribution of gluco-liposomes Cu-labeled with a non-radioactive copper ion. Mice with an A431 tumor and turpentine-induced inflammation received IV administration of glucose-coated $Cu^{2+}$-labeled liposomes. Tumor, inflammation region and organs were collected 3 h after i.v. injection of liposomes (FIG. 7A). Liposomes showed significantly higher accumulation at the tumor as compared to the inflammation region (FIG. 7B).

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. A nanoparticle having a lipid core comprising a plurality of lipids, wherein said lipid core is linked via a first polymeric linker to a 2-Deoxy-D-Glucose (2-DG) molecule and is further linked via a second polymeric linker to a chelating agent; wherein a portion of the lipids attached to said 2-DG-molecules from said plurality of lipids is between about 5 and 20 mol %; wherein a portion of the lipids attached to the chelating agent from said plurality of lipids is between 2.4 and about 10 mol %; and wherein a hydrodynamic diameter of said nanoparticle is between 60 and 200 nm; wherein the first and the second polymeric linkers comprise PEG; and wherein said chelating agent is a metal chelator selected from the group consisting of: 1-(1,3-carboxy-propyl)-4,7,10-(carboxymethyl)-1,4,7,10-tetraazacyclododecane (DOTAGA), 1-(1,2-carboxyethyl)-4,7,10-(carboxymethyl)-1,4,7,10-tetraazacyclododecane (DOTASA) or 1,4,7,10-tetraazaacyclo-dodecane-1,4,7,10-tetra-acetic acid (DOTA), or any combination thereof.

2. The nanoparticle of claim 1, having a specific affinity to a glucose transporter (GLUT) expressing cell.

3. The nanoparticle of claim 1, wherein said chelating agent is bound to a radioactive isotope is selected from the group consisting of: technetium-99m, iodine-123, iodine-131, rhenium-186, rhenium-188, gallium-67, gallium-68, yttrium-90, lutetium-177, copper-64, and any combination thereof.

4. The nanoparticle of claim 1, wherein a weight ratio of any one of (i) said chelating agent or (ii) said 2DG molecule to said nanoparticle is 1:20 to 1:80, respectively.

5. The nanoparticle of claim 1, wherein said nanoparticle is a liposome; and wherein said plurality of lipids comprise a phospholipid and a cholesterol.

6. The nanoparticle of claim 1, wherein said PEG has a molecular weight of between 1 and 10 kDa.

7. The nanoparticle of claim 1, wherein a portion of the lipids attached to the chelating agent from said plurality of lipids is between 5 and about 10 mol %.

8. The nanoparticle of claim 5, wherein said phospholipid comprises one or more compounds selected from the group consisting of: 1,2-distearoyl-sn-glycero-3-phosphoethanolamine (DSPE), 2-Dimyristoyl-sn-glycero-3-phosphorylcholine (DMPC), Dipalmitoylphosphatidylcholine (DPPC), L-α-phosphatidylcholine, hydrogenated soy PC (HSPC), 1,2-dioleoyl-3-trimethylammonium-propane (DOTAP), Sphingomyelin, L-α-phosphatidylserine (Soy).

9. The nanoparticle of claim 5, wherein the lipids attached to the first polymeric linker or to the second polymeric linker are said phospholipids.

10. The nanoparticle of claim 1, wherein (i) said 2-DG molecule is linked to the first polymeric linker and (ii) said chelating agent is linked to the second polymeric linker via amine group or via carboxy group.

11. The nanoparticle of claim 5, wherein a molar ratio between said phospholipid and said cholesterol within said liposome is about 60:30.

12. The nanoparticle of claim 1, wherein said chelating agent is DOTA.

13. A composition comprising a plurality of the nanoparticles of claim 1, wherein said plurality of the nanoparticles are in a form of distinct particles within said composition; wherein a hydrodynamic diameter of at least 95% of said plurality of nanoparticles varies within a range of less than 20%.

14. The composition of claim 13, wherein said composition is configured to accumulate in vivo within a cancer tissue rather than within an inflamed tissue, thereby allowing differentiation between an inflammatory process and a malignant disease of a subject.

15. The composition of claim 13, further comprising a pharmaceutically acceptable carrier.

16. A method of imaging a tumor in a subject in need thereof, the method comprising administering to the subject the composition of claim 13, and performing a diagnostic imaging technique, thereby obtaining an image of said tumor, wherein said tumor comprises glucose transporter (GLUT) overexpressing cells; and wherein the diagnostic imaging technique is positron emission tomography (PET).

17. The method of claim 16, wherein said administering comprises intravenously administering.

18. The method of claim 16, wherein said administering comprises injecting or infusing.

* * * * *